US010188782B2

(12) United States Patent
Yokomizo et al.

(10) Patent No.: US 10,188,782 B2
(45) Date of Patent: Jan. 29, 2019

(54) BLOOD PROCESSING FILTER AND BLOOD PROCESSING METHOD

(71) Applicant: ASAHI KASEI MEDICAL CO., LTD., Tokyo (JP)

(72) Inventors: Tomohisa Yokomizo, Tokyo (JP); Tomoko Uchiyama, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 144 days.

(21) Appl. No.: 15/026,364

(22) PCT Filed: Oct. 2, 2014

(86) PCT No.: PCT/JP2014/076429
§ 371 (c)(1),
(2) Date: Mar. 31, 2016

(87) PCT Pub. No.: WO2015/050216
PCT Pub. Date: Apr. 9, 2015

(65) Prior Publication Data
US 2016/0235904 A1    Aug. 18, 2016

(30) Foreign Application Priority Data

Oct. 2, 2013 (JP) .................................. 2013-207561

(51) Int. Cl.
*B01D 63/00* (2006.01)
*B01D 35/28* (2006.01)
(Continued)

(52) U.S. Cl.
CPC ........ *A61M 1/3636* (2014.02); *A61M 1/0281* (2013.01); *A61M 1/1631* (2014.02);
(Continued)

(58) Field of Classification Search
CPC ........ A61M 2202/0439; A61M 1/3636; A61M 1/0218; A61M 1/3633; A61M 2202/0042;
(Continued)

(56) References Cited

U.S. PATENT DOCUMENTS 4,540,492 A * 9/1985 Kessler ................ B01D 63/085
210/321.75
4,985,153 A    1/1991 Kuroda et al.
(Continued)

FOREIGN PATENT DOCUMENTS

CN    103153357    6/2013
EP    0 526 678    2/1993
(Continued)

OTHER PUBLICATIONS

Search Report issued in PCT/JP2014/076429, dated Jan. 13, 2015.
International Preliminary Report on Patentability issued in PCT/JP2014/076429, dated Apr. 14, 2016.

*Primary Examiner* — Ana M Fortuna
(74) *Attorney, Agent, or Firm* — Greenblum & Bernstein, P.L.C.

(57) ABSTRACT

A blood processing filter comprises an inlet-side flexible container and an outlet-side flexible container that sandwich a filter element, an inlet port, and an outlet port, the filter further comprising: a flow path securing sheet; a first seal portion; and a second seal portion, wherein the flow path securing sheet includes a pair of ribs disposed opposite to each other with the outlet port interposed therebetween, and a slit formed inside of the pair of ribs, and diffusing openings that are disposed outside of the pair of ribs and continuously open from the ribs to the lateral portions of the first seal portion.

23 Claims, 15 Drawing Sheets

(51) Int. Cl.
*A61M 1/34* (2006.01)
*A61M 1/02* (2006.01)
*A61M 1/38* (2006.01)
*A61M 1/36* (2006.01)
*A61M 1/16* (2006.01)

(52) U.S. Cl.
CPC ........ *A61M 1/1652* (2014.02); *A61M 1/3496* (2013.01); *A61M 2202/0439* (2013.01)

(58) Field of Classification Search
CPC ........ B01D 39/1623; B01D 2239/0618; B01D 2239/065; A61L 2/0017; A61B 17/00491
See application file for complete search history.

(56) References Cited

U.S. PATENT DOCUMENTS

| | | |
|---|---|---|
| 5,269,946 A | 12/1993 | Goldhaber et al. |
| 6,032,807 A | 3/2000 | Sternberg et al. |
| 8,881,914 B2 * | 11/2014 | Yokomizo ........... A61M 1/3633 210/435 |
| 9,421,320 B2 * | 8/2016 | Yokomizo ........... A61M 1/3633 |
| 2009/0071905 A1 | 3/2009 | Goudaliez et al. |
| 2011/0192798 A1 | 8/2011 | Goudaliez et al. |
| 2012/0067810 A1 | 3/2012 | Yokomizo et al. |
| 2014/0144832 A1 | 5/2014 | Yokomizo et al. |
| 2016/0235904 A1 * | 8/2016 | Yokomizo ........... A61M 1/0281 |
| 2017/0181426 A1 * | 6/2017 | Wolf ..................... A01N 1/021 |

FOREIGN PATENT DOCUMENTS

| | | |
|---|---|---|
| JP | 1-320064 | 12/1989 |
| JP | 7-267871 | 10/1995 |
| JP | 11-216179 | 8/1999 |
| JP | 2003-512093 | 4/2003 |
| JP | 2005-204781 | 8/2005 |
| JP | 2008-86352 | 4/2008 |
| WO | 92/020428 | 11/1992 |
| WO | 95/017236 | 6/1995 |
| WO | 2012/039400 | 3/2012 |

* cited by examiner

BLOOD PROCESSING FILTER AND BLOOD PROCESSING METHOD

TECHNICAL FIELD

The present invention relates to a blood processing filter for removing undesirable components, such as aggregates and leukocytes, from blood, and to a blood processing method using the blood processing filter. In particular, the present invention relates to a precise and disposable blood processing filter for removing microaggregates and leukocytes which may cause side effects from whole blood preparations, erythrocyte preparations, thrombocyte preparations, blood plasma preparations and the like for blood transfusion, as well as a blood processing method using the blood processing filter.

BACKGROUND ART

It is becoming common for whole blood collected from a donor to be separated into—blood component preparations, such as an erythrocyte preparation, a thrombocyte preparation, and a blood plasma preparation, are separated from whole blood collected from a donor, stored and then provided for transfusion. Since microaggregates and leukocytes included in these blood preparations cause various side effects of blood transfusion, the number of occasions for removing these undesirable components before blood transfusion has been increasing. Particularly, in recent years, the need for leukocyte removal has widely been recognized. The number of countries legislating application of a process of removing leukocytes from all of blood preparations for blood transfusion and subsequent use thereof for transfusion has been increased.

As a method of removing leukocytes from blood preparations, processing blood preparations using a leukocyte removal filter is most typical. Processing the blood preparations using the leukocyte removal filter often performed at the bedside when a blood transfusion operation is performed. In recent years, however, in order to improve quality control of leukocyte-free preparations and the effectiveness of leukocyte removal process, it is more common, particularly in developed countries, to process the blood preparations in blood centers before storing the blood preparations (pre-storage leukocyte removal).

A blood collection-separation set typically consisting of two to four flexible bags, a tube connecting these bags, an anticoagulant, an erythrocyte preservation solution, a blood collection needle and the like has been used for collecting blood from a donor, separation into a plurality of blood components, and storing the blood components. A system in which a leukocyte removal filter is incorporated into such a blood collection-separation set has been widely used as a suitable system for use in the aforementioned "pre-storage leukocyte removal", and is referred to as a "closed system", an "integrated system" or the like. These systems are disclosed in Japanese Unexamined Patent Publication No. H1-320064, International Publication No. WO 92/020428 and the like.

Conventionally, a filter element made of nonwoven fabric or a porous body packed in a hard container of polycarbonate or the like has been widely used as a leukocyte removal filter. However, since the container has a low gas permeability, there is a problem that it is difficult to apply steam sterilization, which is widely used as a sterilization process for blood collection-separation sets. In one type of the closed system, leukocytes are first removed from the whole blood preparation after blood collection, the leukocyte removal filter is separated, and then a centrifugal operation for component separation is applied. In another case, first, a plurality of blood components are separated by centrifuging the whole blood, and subsequently the leukocytes are removed. In the latter case, the leukocyte removal filter is also centrifuged together with the blood collection-separation set. At such time, a hard container may damage bags and tubes, or the hard container itself may not withstand the stress and may break during centrifugation.

As a method for solving these problems, flexible leukocyte removal filters have been developed in which a material having excellent flexibility and steam permeability identical or similar to the material used for the bags of the blood collection-separation set is used for the container. These flexible leukocyte removal filters that adopt a container made of a material having excellent flexibility and steam permeability can be broadly classified into a type in which the filter element is once welded to a sheet-shaped flexible frame, and subsequently the filter is welded to a housing material (see Description of European Patent No. 0526678 and Japanese Unexamined Patent Publication No. H11-216179), and a type in which a flexible container is directly welded to the filter element (see Japanese Unexamined Patent Publication No. H7-267871 and International Publication No. WO 95/017236). Hereinafter, the former is sometimes referred to as a frame welding type and the latter is sometimes referred to as a container welding type.

Typically, in the case of processing blood with these types of leukocyte removal filters, a bag that contains a blood preparation to be processed and is connected to a blood inlet side of the filter via a tube is placed at a height that is approximately 20 to 100 cm above the filter to allow the blood preparation to pass through the filter by the action of gravity. The filtered blood preparation is stored in a recovery bag connected to a blood outlet side of the filter via a tube. During filtration, a pressure loss occurs due to the resistance of the filter element, whereby the pressure in a space on the inlet side of the filter becomes a positive pressure. In the case of the filter that includes a flexible container, there is a tendency for the flexibility of the container itself to cause the container to swell like a balloon due to the positive pressure, thereby pressing the filter element against the container on the outlet side.

Furthermore, typically, a bag for storing blood having been processed with the blood filter is placed at a position that is 50 to 100 cm lower than the filter. Since blood moves through a flow path on the downstream side due to the action of gravity, there is a tendency for the outlet side of the filter to become a negative pressure, and the flexible container is prone to be in close contact with the filter element.

That is, it has been pointed out previously that a filter adopting a flexible container has a problem in that there is a strong tendency for the filter element to be in close contact with the outlet-side container due to the dual force, and thus the flow of blood is impeded and an adequate flow rate cannot be obtained.

To address the problem, a blood processing filter including a flow path securing sheet disposed between a filter element and an outlet-side flexible container has been proposed (International Publication No. WO 2012/039400). The flow path securing sheet is provided with a plurality of slit-shaped flow path holes formed by cutting the sheet. Consequently, even if a dual force is applied during filtration, a blood flow path is secured between the flow path holes in the flow path securing sheet and the outlet port, and a sufficient flow rate can be obtained.

CITATION LIST

Patent Literature

[Patent Literature 1] Japanese Unexamined Patent Publication No. H01-320064
[Patent Literature 2] International Publication No. WO 92/020428
[Patent Literature 3] Description of European Patent No. 0526678
[Patent Literature 4] Japanese Unexamined Patent Publication No. H11-216179
[Patent Literature 5] Japanese Unexamined Patent Publication No. H07-267871
[Patent Literature 6] International Publication No. WO 95/017236
[Patent Literature 7] International Publication No. WO 2012/039400

SUMMARY OF INVENTION

Technical Problem

There were, however, a problem in that according to the conventional blood processing filter including the flow path securing sheet, the blood preparation remains at parts along ribs that are between the flow path holes in the flow path securing sheet, thereby reducing the blood preparation collecting rate.

Thus, the present invention has an object to provide a blood processing filter that can improve the blood preparation collecting rate without reducing filtering flow rate.

Solution to Problem

In order to solve the problems, the inventors have researched the shapes of the flexible container of the blood processing filter, the filter element, flow path securing sheet and the like, and succeeded in solving the problem by inventing a blood processing filter that can improve the blood preparation collecting rate without degrading the advantages of arranging the flow path securing sheet.

That is, an aspect of the present invention is a blood processing filter comprising a sheet-shaped filter element, an inlet-side flexible container and an outlet-side flexible container that sandwich the filter element, an inlet port that is provided at the inlet-side flexible container and receives unprocessed blood, an outlet port that is provided at the outlet-side flexible container and discharges the blood processed by the filter element, the filter further comprising: a flow path securing sheet disposed between the filter element and the outlet-side flexible container; a belt-shaped first seal portion that seals at least the filter element and the flow path securing sheet, and is provided so as to be apart from the outlet-side flexible container; and an annular second seal portion that seals at least the inlet-side flexible container and the outlet-side flexible container, and is provided so as to surround the filter element and the flow path securing sheet, wherein the first seal portion includes a pair of lateral portions disposed opposite to each other with the outlet port interposed therebetween, and a communication portion connected to the pair of lateral portions, and the flow path securing sheet includes a pair of ribs that are disposed inside of the pair of lateral portions and opposite to each other with the outlet port interposed therebetween, a slit disposed inside of the pair of ribs to communicate with a concave portion formed of the communication portion, and diffusing openings that are disposed outside of the pair of ribs and continuously open from the ribs to the lateral portions and communicate with a concave portion formed of the lateral portions. Note that, blood according to the present invention includes blood preparations, such as whole blood preparations, erythrocyte preparations, thrombocyte preparations and blood plasma preparations, for blood transfusion. Furthermore, capability of communication according to the present invention refers to, when a state in which blood is flowing is assumed, or when blood is actually flowing, a continuous gap where the outlet-side flexible container and another element are not in close contact with each other can be formed.

According to this blood processing filter, even when the dual force of a positive pressure on the inlet side and a negative pressure on the outlet side is applied during filtration, the pair of ribs of the flow path securing sheet prevent close contact in proximity to the outlet port, and the slit formed in the pair of ribs secures the flow path to the outlet port. As a result, impediment of flows and reduction in filtering performance are avoided. Moreover, since the diffusing openings are provided, a large range continuous from the ribs to the lateral side portions can be used as an effective filtering surface, which makes blood preparation resistant to being stagnant, and can improve the blood preparation collecting rate.

Furthermore, according to the blood processing filter, the pair of ribs may be a straight line, a bent line, a curve, or any combination thereof.

Furthermore, according to the blood processing filter, the communication portion may include a pair of side portions disposed opposite to each other with the outlet port interposed therebetween, and the slit may communicate with a concave portion formed of the pair of side portions.

Furthermore, according to the blood processing filter, the pair of ribs may have distal ends connected to each other so as to surround the outlet port.

Furthermore, according to the blood processing filter, in the filter element, the effective filtering area of a filtering portion may be $20 \times 10^{-4}$ m$^2$ to $70 \times 10^{-4}$ m$^2$.

Furthermore, according to the blood processing filter, in the flow path securing sheet, the ratio of the total area of the slit and the diffusing openings to the effective filtering area of the filtering portion of the filter element may be 30% to 97%.

Furthermore, according to the blood processing filter, the interval between the pair of ribs may be 0.1 to 2 times as large as the width of the outlet opening of the outlet port.

Furthermore, according to the blood processing filter, the interval of the pair of ribs may be 0.5 to 10 mm.

Furthermore, according to the blood processing filter, a post-filter layer for securing a flow toward the outlet port may be disposed on a side of the filter element nearer to the flow path securing sheet.

Furthermore, according to the blood processing filter, the post-filter layer may be a filter layer formed by stacking one or more sheets of nonwoven fabric with an air permeability of 180 to 300 cc/cm$^2$/sec. and a thickness of 0.2 to 2.0 mm.

Furthermore, according to the blood processing filter, the second seal part may sandwich and be in close contact with the flow path securing sheet between the inlet-side flexible container and the outlet-side flexible container.

Furthermore, according to the blood processing filter, the first seal part may sandwich and be in close contact with the filter element between the inlet-side flexible container and the flow path securing sheet.

Furthermore, according to the blood processing filter, the thickness of the flow path securing sheet may be 0.1 to 3.5 mm.

Furthermore, according to the blood processing filter, a frame sheet having an opening may be disposed between the filter element and the inlet-side flexible container.

Furthermore, according to the blood processing filter, the first seal portion may be formed by sealing the frame sheet, the filter element and the flow path securing sheet in a belt-shaped manner in a state where the flume sheet and the flow path securing sheet sandwich the filter element.

Furthermore, according to the blood processing filter, the frame sheet and the flow path securing sheet may have an identical shape, and be rotationally symmetric to allow the inlet-side container and the outlet-side container to be used in a manner replaced with each other.

Furthermore, according to the blood processing filter, the distance from an end of the slit to an end of the communication portion nearer to the slit may be 0 to 4 mm.

Furthermore, according to the blood processing filter, the distance from an end of the diffusing opening to an end of the lateral portion of the first seal portion nearer to the diffusing opening may be 0 to 4 mm.

Furthermore, it is preferred that the average processing speed of the blood processing filter be at least 12.0 g/min. Preferably, the average processing speed is at least 15.0 g/min., more preferably, at least 17.0 g/min.

The average processing speed is an average processing speed calculated from the amount of recovery and the total processing time when liquid to be processed is used instead of the blood, 300 g of the liquid to be processed is injected into the liquid reservoir bag before filtration and subsequently 15 mL of air is injected, and the total head that is a total of a upstream-side head from the liquid reservoir bag to the inlet of the blood processing filter, a head from the inlet of the blood processing filter to the outlet, and a downstream-side head from the outlet of the blood processing filter to the liquid recovery bag, is fixed to 150 cm, and the liquid is caused to flow by gravity at room temperature. Moreover, the liquid to be processed is polyvinylpyrrolidone aqueous solution with a weight-average molecular weight of 360000 prepared to have a viscosity of 17 mPas and pH 3.8 at a temperature of 25° C.

Furthermore, according to the blood processing filter, it is preferred that the remaining amount of liquid remaining in the blood processing filter after processing be 30.0 g or less. Preferably, the remaining amount is 28.0 g or less, and more preferably, 26.0 g or less.

The remaining amount is an amount of liquid to be processed that remains in the blood processing filter after completion of processing (after completion of filtration), in the case where liquid to be processed is used instead of the blood, 300 g of the liquid to be processed is injected into the liquid reservoir bag before filtration and subsequently 15 mL of air is injected, and the total head that is a total of a upstream-side head from the liquid reservoir bag to the inlet of the blood processing filter, a head between the inlet and outlet of the blood processing filter, and a downstream-side head from the outlet of the blood processing filter to the liquid recovery bag, is fixed to 150 cm, and the liquid is caused to flow by gravity at room temperature. Moreover, the liquid to be processed is polyvinylpyrrolidone aqueous solution with a weight-average molecular weight of 360000 prepared to have a viscosity of 17 mPa·s and pH 3.8 at a temperature of 25° C.

Furthermore, another aspect of the present invention is a blood processing method using a blood processing filter, the blood processing filter comprising a sheet-shaped filter element, an inlet-side flexible container and an outlet-side flexible container that sandwich the filter element, an inlet port that is provided at the inlet-side flexible container and receives unprocessed blood, an outlet port that is provided at the outlet-side flexible container and discharges the blood processed by the filter element, the filter further comprising: a flow path securing sheet disposed between the filter element and the outlet-side flexible container; a belt-shaped first seal portion that seals at least the filter element and the flow path securing sheet, and is provided so as to be apart from the outlet-side flexible container; and an annular second seal portion that seals at least the inlet-side flexible container and the outlet-side flexible container, and is provided so as to surround the filter element and the flow path securing sheet, wherein the first seal portion includes a pair of lateral portions disposed opposite to each other with the outlet port interposed therebetween, and a communication portion connected to the pair of lateral portions, and the flow path securing sheet includes a pair of ribs that are disposed inside of the pair of lateral portions and opposite to each other with the outlet port interposed therebetween, a slit disposed inside of the pair of ribs to communicate with a concave portion formed of the communication portion, and diffusing openings that are disposed outside of the pair of ribs, continuously open from the ribs to the lateral portions and communicate with a concave portion formed of the lateral portions.

Furthermore, the blood processing filter includes a post-filter layer for securing a flow toward the outlet port, on a side of the filter element nearer to the flow path securing sheet; in the blood processing method using the blood processing filter, it is preferred that, from among flows of the blood flowing in the post-filter layer, a flow in a direction toward the outlet port is formed in a region overlaid on the slit, and a flow more diffusing than that in the region overlaid on the slit is formed in a region overlaid on the diffusing openings.

Furthermore, it is preferred that leukocytes be removed by the blood processing method.

Advantageous Effects of Invention

According to the present invention, the blood preparation collecting rate can be improved without reducing the filtering flow rate.

DESCRIPTION OF EMBODIMENTS

Embodiments of the present invention are described hereunder with reference to the drawings. Note that the term, blood, described in each of the following embodiments includes blood preparations such as whole blood preparations, erythrocyte preparations, thrombocyte preparations and blood plasma preparations for blood transfusion. Furthermore, although various modes can be adopted for the external shape of the blood processing filter, such as a rectangular shape, a disc shape, an oval disc shape, and an elliptical shape, a rectangular shape is preferable for decreasing loss of materials during production. Accordingly, in the following embodiments, an example in which the blood processing filter has a rectangular shape is described. In each diagram, the identical or corresponding portions are assigned the same symbols, and redundant description is omitted.

Figure 1:
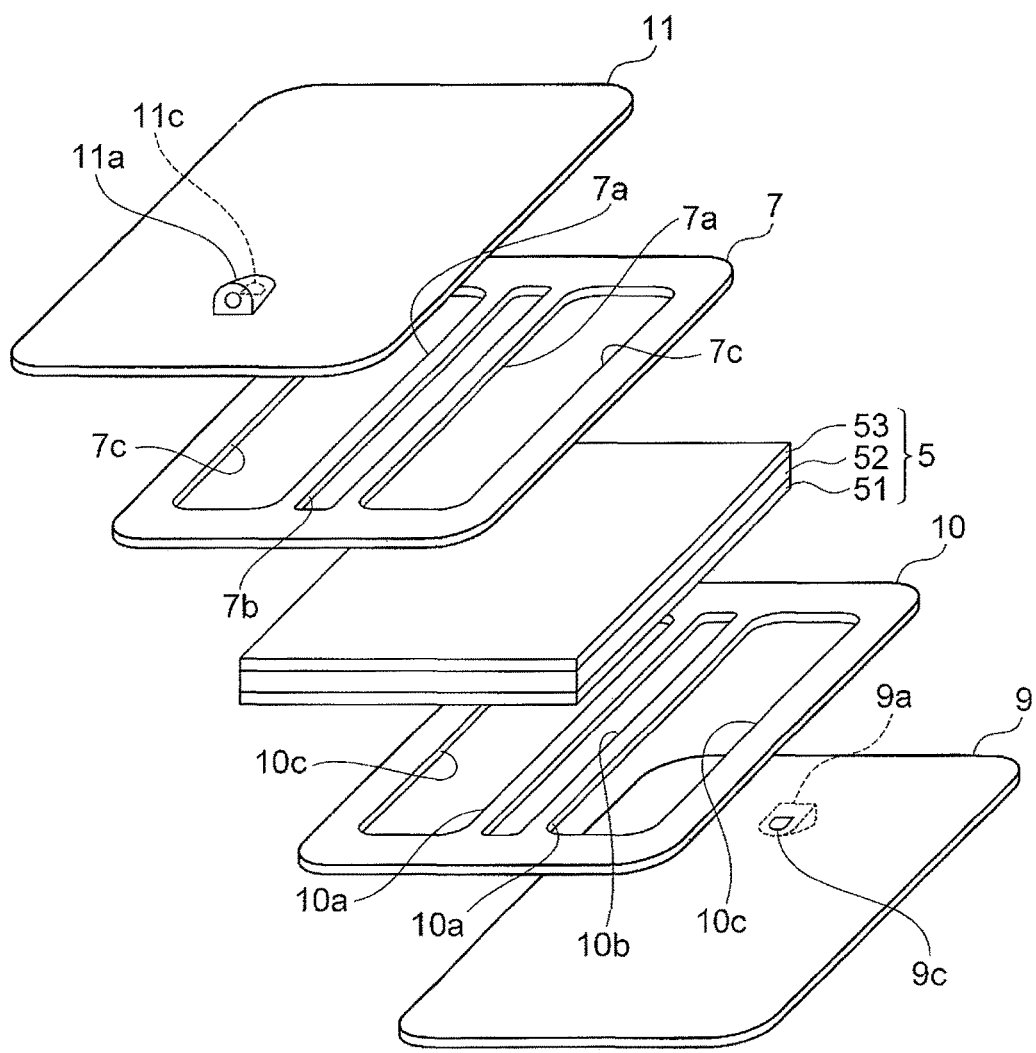
FIG. 1 is an exploded perspective view of a blood processing filter according to a first embodiment.

First, referring to FIG. 1, members forming a blood processing filter 1A according to a first embodiment of the present invention are described. As shown in FIG. 1, the blood processing filter 1A includes elements that are an inlet-side container (inlet-side flexible container) 9, a frame sheet 10, a filter element 5, a flow path securing sheet 7, and an outlet-side container (outlet-side flexible container) 11.

The inlet-side container 9 has a rectangular sheet shape. An inlet port 9a that receives unprocessed blood when an inlet-side circuit 102 (see FIG. 10) allowing blood to flow is formed is sealed at the inlet-side container 9. An inlet flow path 9b (see FIGS. 2 and 3) that accepts unprocessed blood is formed in the inlet port 9a. Furthermore, an inlet opening 9c that allows the inlet flow path 9b and the inside of the inlet-side container 9 to communicate with each other is formed in the inlet port 9a. Note that the term, (to) seal, refers to fixing by adhesion (including welding) to an extent that can prevent liquid from leaking.

The frame sheet 10 is disposed between the inlet-side container 9 and the filter element 5. The frame sheet 10 is a rectangular sheet, and includes a pair of ribs 10a disposed opposite to each other with the inlet port 9a interposed therebetween, a slit-shaped first opening (opening) 10b formed inside of the pair of ribs 10a, and two second openings (openings) 10c formed outside of the pair of ribs 10a.

The filter element 5 is disposed between the frame sheet 10 and the flow path securing sheet 7. The filter element 5 has a rectangular sheet shape with a predetermined thickness. The filter element 5 has a configuration where a prefilter layer 51, a main filter layer 52, and a post-filter layer 53 are stacked in this order from the element nearer to the inlet-side container 9.

The flow path securing sheet 7 is disposed between the filter element 5 and the outlet-side container 11. The flow path securing sheet 7 is a rectangular sheet, and includes a pair of ribs 7a disposed opposite to each other with the outlet port 11a interposed therebetween, a slit 7b formed inside of the pair of ribs 7a, and two diffusing openings 7c formed outside of the pair of ribs 7a. The flow path securing sheet 7 has the same shape as the frame sheet 10.

The outlet-side container 11 has a rectangular sheet shape. The outlet port 11a is sealed at the outlet-side container 11. An outlet flow path 11b (see FIGS. 2 and 3) for discharging blood processed by the filter element 5 when an outlet-side circuit 104 (see FIG. 10) allowing blood to flow is formed is formed at the outlet port 11a. Furthermore, an outlet opening 11c that allows the outlet flow path 11b and the inside of the outlet-side container 11 to communicate with each other is formed at the outlet port 11a. The outlet-side container 11 has the same shape as the inlet-side container 9.

Figure 2:
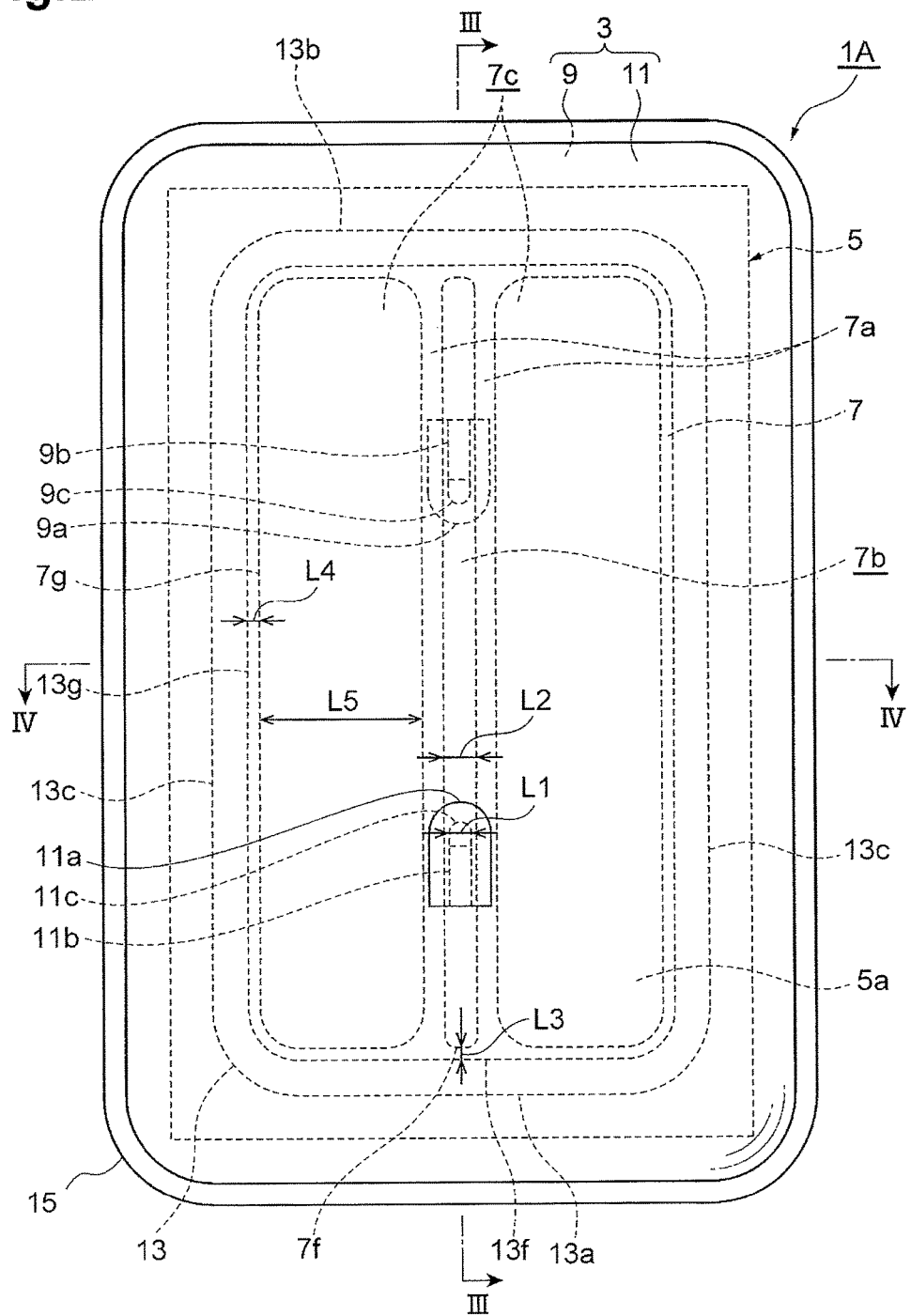
FIG. 2 is a plan view of the blood processing filter.
Figure 3:
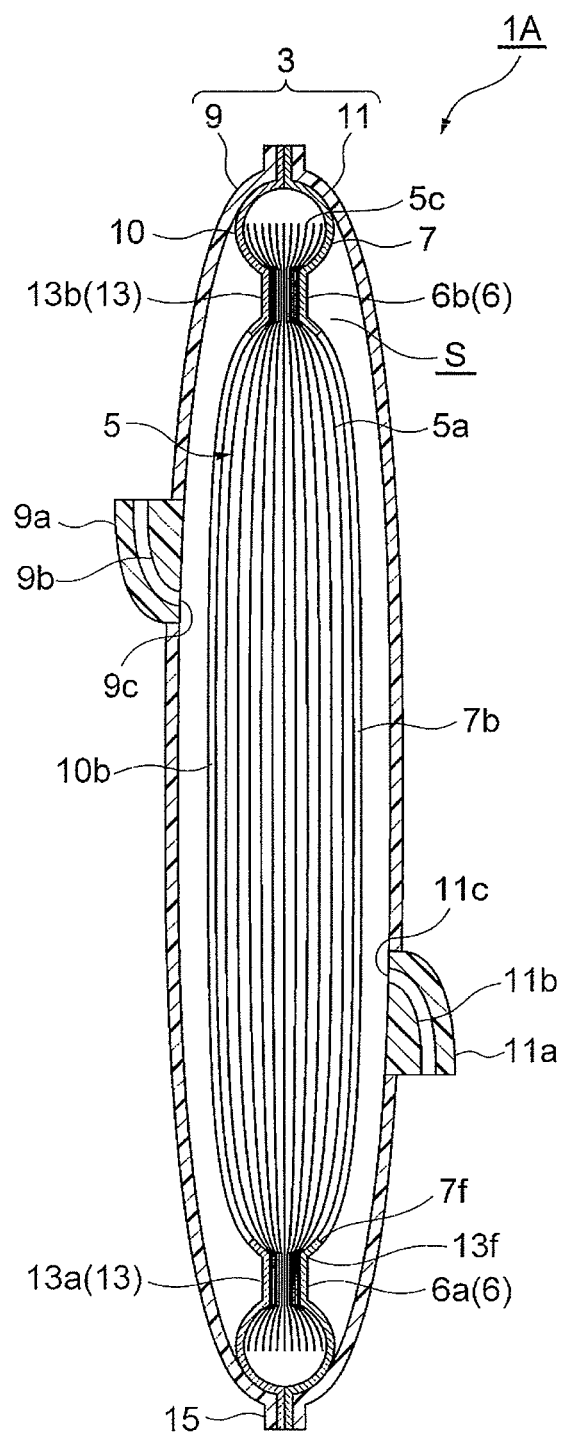
FIG. 3 is a longitudinal sectional view taken along line III-III of FIG. 2.
Figure 4:
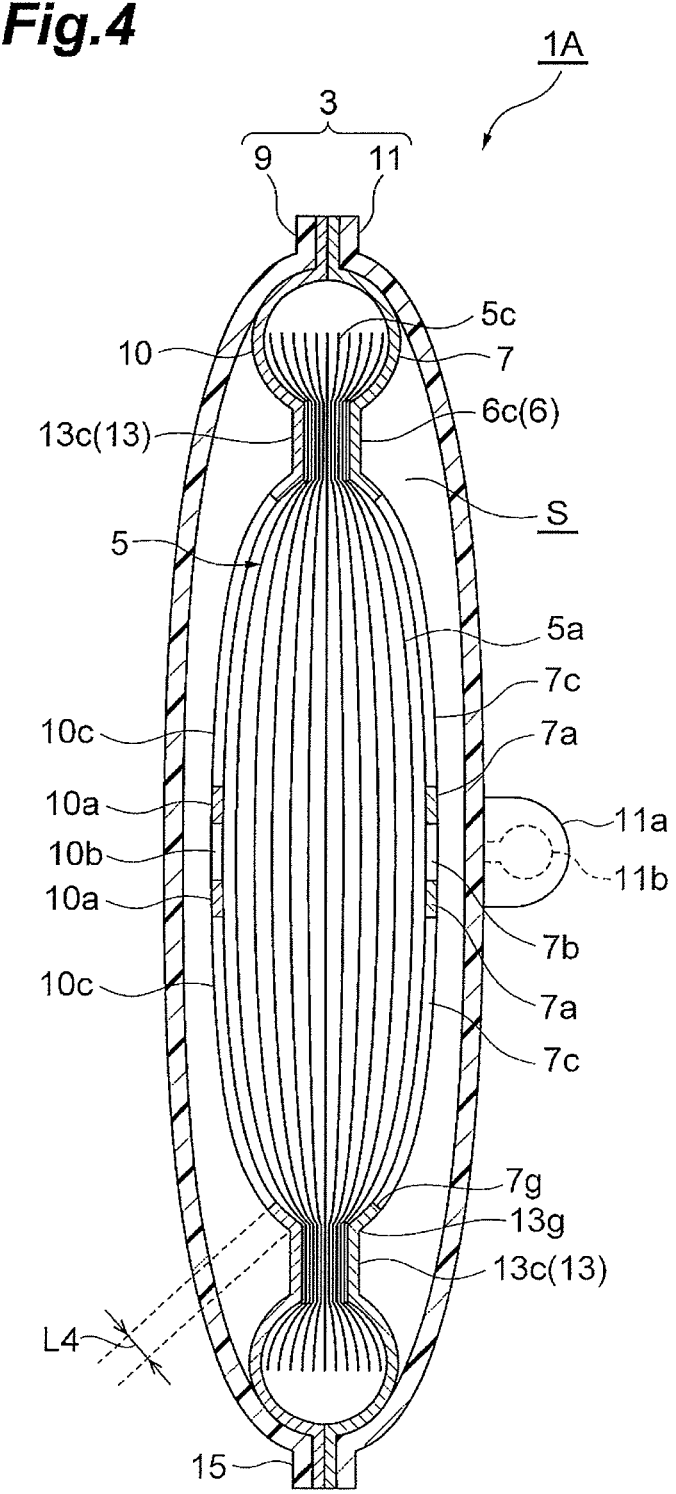
FIG. 4 is a cross sectional view taken along line IV-IV of FIG. 2.

First, referring to FIGS. 2, 3 and 4, the blood processing filter 1A is described. The blood processing filter 1A includes a flexible container 3. The flexible container 3 includes the inlet-side container 9 and the outlet-side container 11 that sandwich the filter element 5. The flexible container 3 is a container with a rectangular and flat shape; the flat shape means a shape having a small thickness and a wide surface.

The flow path securing sheet 7 and the frame sheet 10 are sealed along the periphery of the filter element 5 in a state where the filter element 5 is clamped between. A belt-shaped adhesive region along the periphery of the filter element 5 is an inner seal portion (first seal portion) 13. The inner seal portion 13 is provided so as to be apart from each of the inlet-side container 9 and the outlet-side container 11.

The inner seal portion 13 surrounds the inlet port 9a and the outlet port 11a in a rectangular and circular manner, and includes a lower side portion (communication portion) 13a, an upper side portion (communication portion) 13b, and a pair of lateral side portions (lateral portions) 13c. The pair of lateral side portions 13c are disposed opposite to each other with the inlet port 9a and the outlet port 11a interposed therebetween. The lower side portion 13a and the upper side portion 13b are disposed opposite to each other with the inlet port 9a and the outlet port 11a interposed therebetween, and connected to opposite ends of the pair of lateral side portions 13c.

Figure 6:
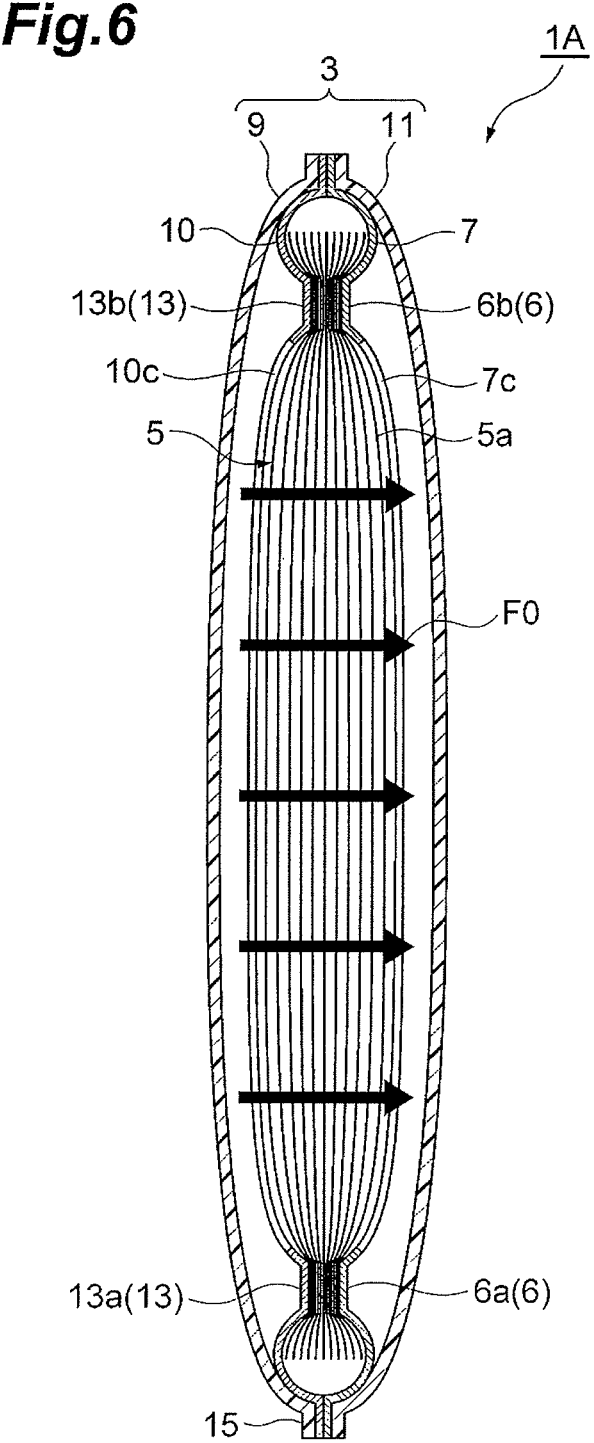
FIG. 6 is a longitudinal sectional view taken along line VI-VI of FIG. 5.
Figure 7:
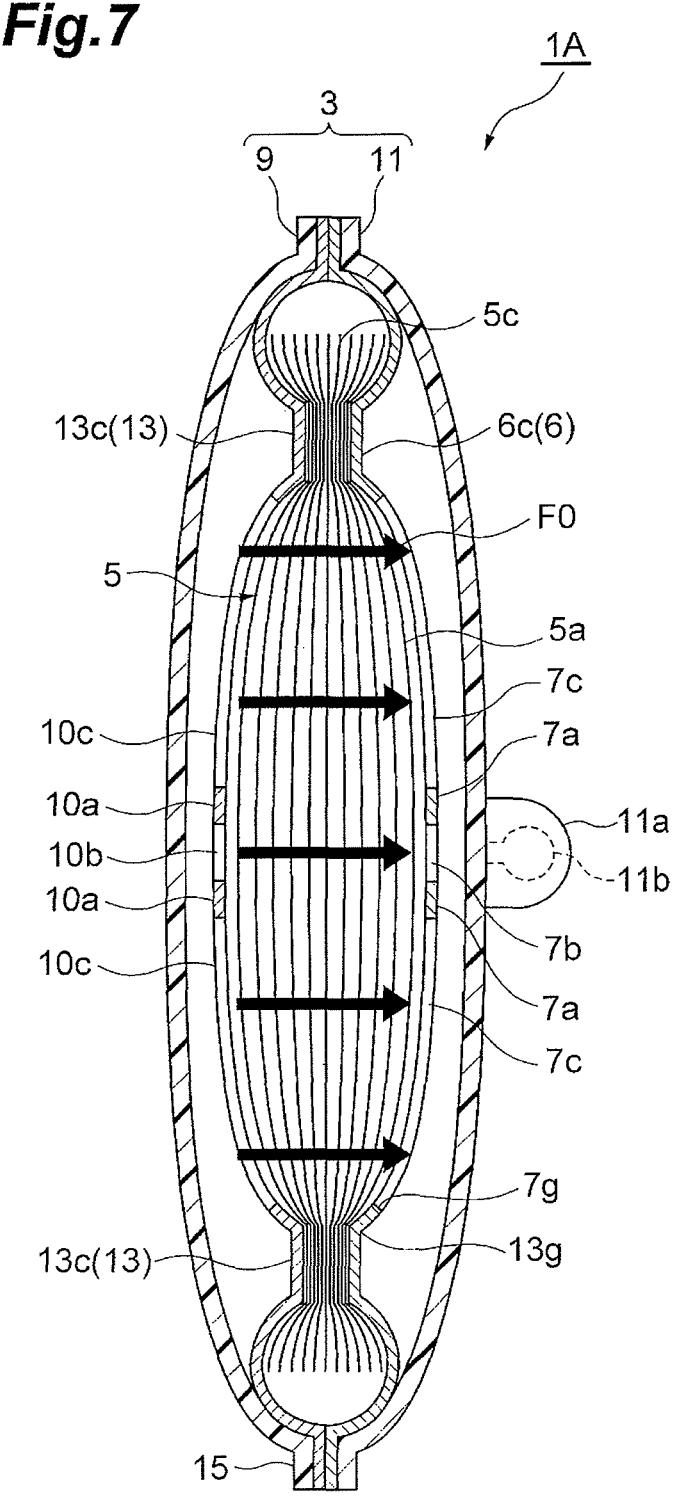
FIG. 7 is a cross sectional view taken along line VII-VII of FIG. 5.

A region inside of the inner seal portion 13 in the flexible container 3 serves as a filtering portion that allows blood to flow, and a part of the filter element 5 facing the filtering portion serves as an effective filtering portion 5a (see FIGS. 6 and 7). The area of the effective filtering portion 5a (effective filtering area) is $20 \times 10^{-4}$ to $70 \times 10^{-4}$ m$^2$, preferably, $35 \times 10^{-4}$ to $60 \times 10^{-4}$ m$^2$, more preferably, $40 \times 10^{-4}$ to $55 \times 10^{-4}$ m$^2$, and further preferably $40 \times 10^{-4}$ to $45 \times 10^{-4}$ m$^2$. An effective filtering area smaller than $20 \times 10^{-4}$ m$^2$ causes a possibility of degrading the blood preparation collecting rate and increasing the filtering time. On the other hand, the area exceeding $70 \times 10^{-4}$ m$^2$ causes a possibility of degrading the blood preparation collecting rate. Note that a protruding nonwoven fabric portion 5c that is an end portion of the filter element 5 protrudes to the outside of the inside seal portion 13 in the flexible container 3.

The peripheries of the inlet-side container 9 and the outlet-side container 11 overlap with the peripheries of the frame sheet 10 and the flow path securing sheet 7, and are sealed in a belt shape to thereby form an rectangular and annular outside seal portion (second seal portion) 15. That is, the outside seal portion 15 sandwiches and is in close contact with the flow path securing sheet 7 and the frame sheet 10 between the inlet-side container 9 and the outlet-side container 11. Although the inner seal portion 13 and the outside seal portion 15 may be formed using high frequency welding, the scope is not limited thereto. Any adhesion technique, such as ultrasonic welding or thermal welding, can be used.

The outlet side of the filter element 5 and the flow path securing sheet 7 is provided with a rectangular and annular concave portion 6 formed corresponding to the inner seal portion 13. The concave portion 6 includes a lower side concave portion 6a formed of the lower side portion 13a, an upper side concave portion 6b formed of the upper side portion 13b, and lateral side concave portions 6c formed of lateral side portions 13c.

The inlet-side container 9 and the outlet-side container 11 do not adhere to the inner seal portion 13, and are provided so as to be apart from the inner seal portion 13 in a stationary state. The outlet-side container 11 has an expansion and contraction margin to some extent, but is not made of a material expandable without limitation. Consequently, even in a state where blood is flowing (outlet-side negative pressure state), formation of the concave portion 6 in proximity to the inner seal portion 13 allows a blood passage region S (see FIGS. 8 and 9) to be secured without the outlet-side container 11 being adhering to and in contact with the filter element 5 and the flow path securing sheet 7.

The flow path securing sheet 7 includes the pair of ribs 7a, the slit 7b, and the two diffusing openings 7c, in the inside of the inner seal portion 13. The slit 7b is inside of the pair of ribs 7a, and the two diffusing openings 7c are outside of the pair of ribs 7a. With respect to the width L1 of the outlet opening 11c, the pair of ribs 7a is formed such that a rib opening width, i.e., the width L2 of the slit 7b (the interval of pair of ribs 7a) is substantially identical to the width L1 of the outlet opening 11c. The diffusing opening 7c is formed to have a width L5. Preferably, the width L2 of the slit 7b is 0.1 to 2 times as large as the width L1 of the outlet opening 11c. Preferably, the width L2 of the slit 7b is, for example, 0.5 to 10 mm, and more preferably, 1 to 5 mm. Preferably, the width L5 of the diffusing opening 7c is 5 to 40 mm, 20 to 35 min, or 20 to 30 mm.

The pair of ribs 7a are disposed inside of the pair of lateral side portions 13c and opposite to each other with the outlet port 11a interposed therebetween, and continuous from the lower side portion 13a to the upper side portion 13b. Each of the slit 7b and the two diffusing openings 7c continuously opens from the lower side portion 13a to the upper side portion 13b. As a result, each of the slit 7b and the two diffusing openings 7c communicates with both the lower side concave portion 6a and the upper side concave portion 6b. Furthermore, the two diffusing openings 7c continuously open from the ribs 7a to the lateral side portions 13c. Consequently, the diffusing openings 7c also communicate with the respective lateral side concave portions 6c. Note that the communication of the slit 7b and the diffusing openings 7c with the concave portion 6 means that the blood flow path formed of the slit 7b and the diffusing openings 7c faces the passage region S formed of the concave portion 6, and blood freely enters and exits between the slit 7b and the passage region S and between the diffusing openings 7c and the passage region S.

Thus, the flow path securing sheet 7 has a shape of being cut off except the two ribs 7a at an inner portion surrounded by the inner seal portion 13. As a result, the slit 7b and the two diffusing opening 7c are formed. The ratio of the total area of the slit 7b and the two diffusing openings 7c to the area of the effective filtering portion 5a of the filter element 2 is 30% to 97%, preferably, 50% to 97%, more preferably, 60% to 97%, and further preferably, 80% to 97%. The ratio less than 30% causes a possibility that the blood preparation collecting rate is degraded even if the filtering flow rate can be secured. The ratio exceeding 97% makes the ribs 7a too narrow, which is prone to causing malfunctions, such as falling and twisting, and increases the possibility of degrading the function of the ribs 7a for securing the flow path. Furthermore, the sufficient strength of ribs 7a cannot be obtained. Manufacturing and maintenance of the shape become difficult. Note that the frame sheet 10 has the same shape.

In this embodiment, the outlet port 11a is disposed to be overlaid on the slit 7b. Consequently, the outlet port 11a can communicate with the blood passage region S formed of the concave portion 6 (see FIGS. 8 and 9) through the slit 7b in a state of allowing blood to flow (outlet-side negative pressure state). The slit 7b and the diffusing openings 7c communicate with each other through the passage region S so as to allow blood to freely enter and exit, which stably maintain flowing in and out of blood (see FIG. 5).

The inlet port 9a sealed at the inlet-side container 9 can be appropriately disposed in an inner region of the inner seal portion 13. The inlet port 9a according to this embodiment is disposed at a position that is the center between the pair of lateral side portions 13c of the inner seal portion 13 and is nearer to the upper side portion 13b than to the lower side portion 13a. That is, the inlet port 9a according to this embodiment is disposed on the upper side in a state where the blood processing filter 1A is placed upright for blood processing. However, the placement is not limited thereto.

The outlet port 11a sealed at the outlet-side container 11 can be appropriately disposed in an inner region of the inner seal portion 13 only if the port is at a position between the pair of ribs 7a. The outlet opening 11c of the outlet port 11a is disposed such that at least a part thereof is overlaid on the slit 7b of the flow path securing sheet 7 in a plan view. Consequently, the blood efficiently flows, which allows the filter element 5 as a filter material to be effectively utilized. The outlet port 11a according to this embodiment is disposed at a position that is the center between the pair of lateral side portions 13c of the inner seal portion 13 and is nearer to the lower side portion 13a than the upper side portion 13b. That is, the outlet port 11a according to this embodiment is disposed on the lower side in a state where the blood processing filter 1A is placed upright for blood processing. However, the placement is not limited thereto.

Figure 5:
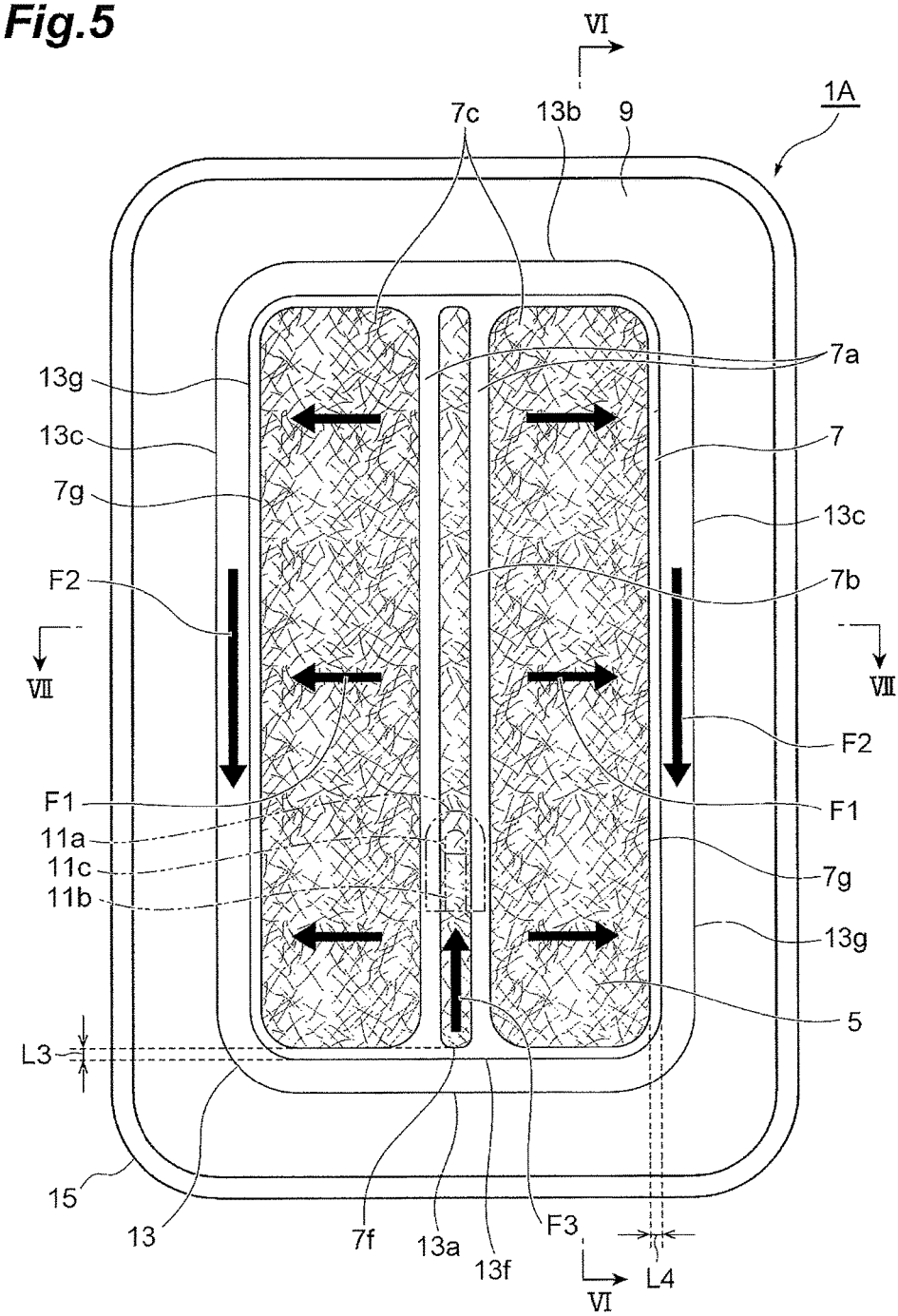
FIG. 5 is a view that schematically shows a flow of blood in an outlet-side container.

Next, referring to FIGS. 5 to 7, blood flows in the blood processing filter 1A are described. Blood flows F0 having uniformly passed through the filter element 5 flow from the slit 7b and the diffusing openings 7c into the outlet-side container 11. Subsequently, from the diffusing openings 7c, blood flows F1 toward the passage region S secured by the lateral side concave portion 6c are formed. Subsequently, blood flows F2 from the lateral side concave portions 6c through the passage region S toward the lower side concave portion 6a are formed. Furthermore, blood flows F3 from the passage region S toward the outlet port 11a through the slit 7b are formed.

Figure 8:
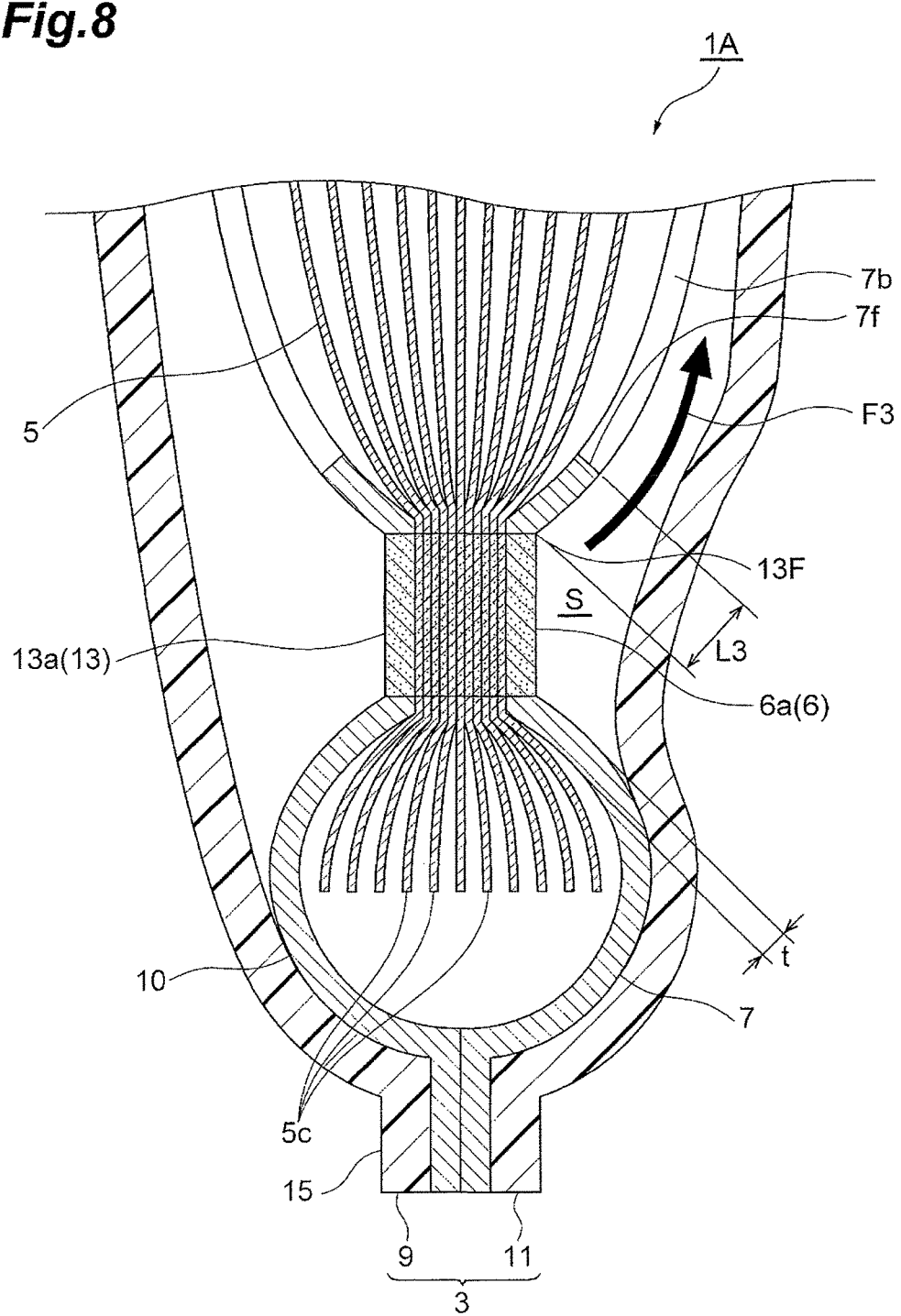
FIG. 8 is an enlarged sectional view of a lower side portion and its proximity in the case where the distance from the end of a slit to the slit-side end of the lower side portion is relatively small.
Figure 9:
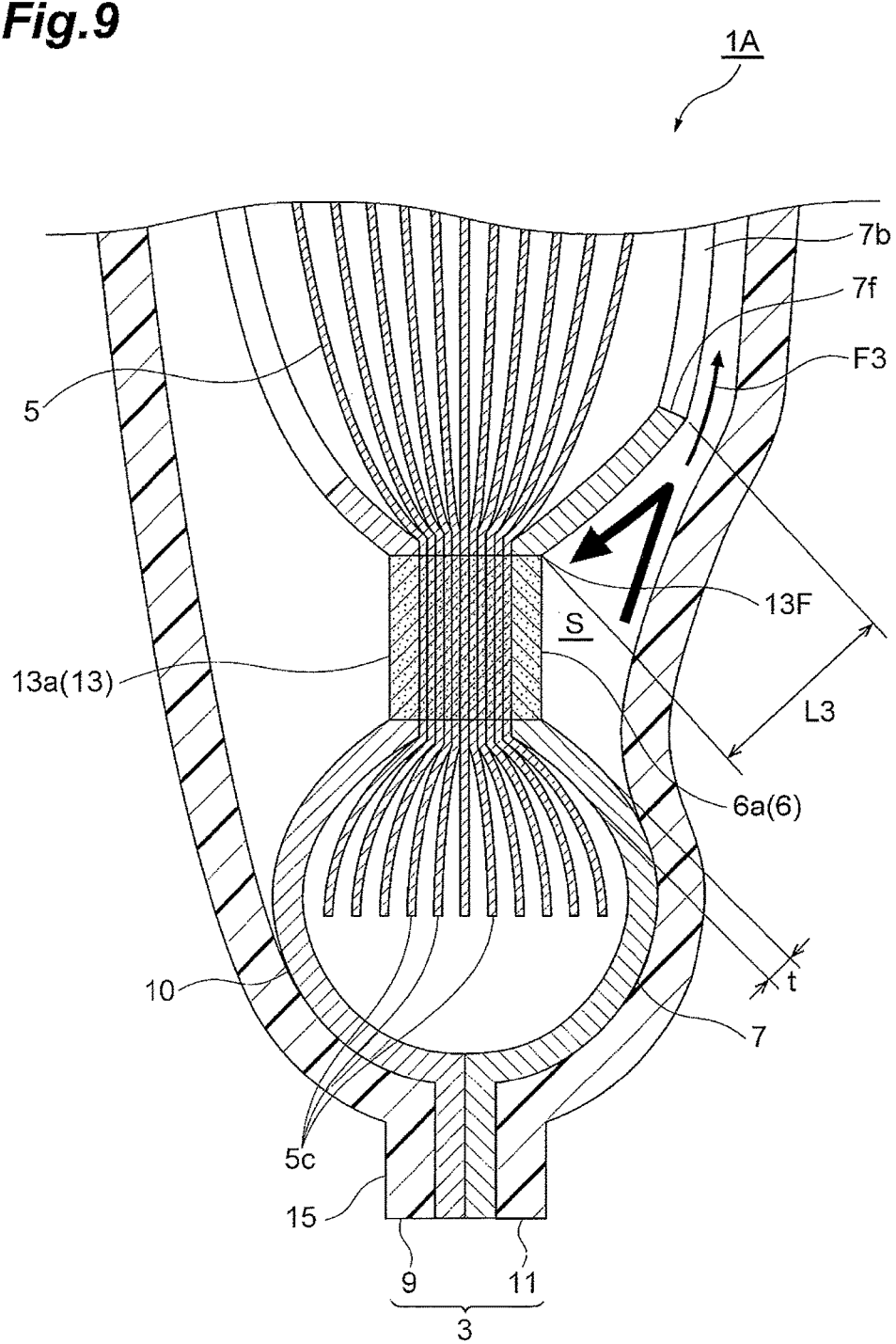
FIG. 9 is an enlarged sectional view of a lower side portion and its proximity in the case where the distance from the end of a slit to the slit-side end of the lower side portion is relatively long.

Here, referring to FIGS. 8 and 9, the relationship between the distance L3 from the end 7f of the slit 7b to the end 13f of the lower side portion 13a nearer to the slit 7b and the flow rate is described. FIGS. 8 and 9 are sectional view showing the proximity around the lower side portion 13a of the inner seal portion 13 in the state of allowing blood to flow (outlet-side negative pressure state) in enlarged manners. FIG. 8 shows the case where the distance L3 is relatively short. FIG. 9 shows the case where the distance is relatively long.

In proximity to the lower side portion 13a, the lower side concave portion 6a is formed. As a result, the outlet-side container 11 is prevented from easily adhering to and coming into contact with the filter element 5, thereby securing the passage region S. Next, as to the relationship between the blood flows F3 from the passage region S toward the outlet port 11a and the distance L3, the distance L3 is short in the embodiment shown in FIG. 8. Consequently, it is relatively difficult for the flow path securing sheet 7 to prevent the flows F3. In the embodiment shown in FIG. 9, the distance L3 is long. Consequently, it is relatively easy for the flow path securing sheet 7 to prevent the flows F3. That is, when the distance L3 exceeds a predetermined range, there is a possibility of preventing blood from effectively flowing even with the secured passage region S.

Here, in view of stably maintaining the flow rate of the blood flow F3, it is preferable that the distance L3 be small (short). That is, in the area of the slit 7b, the larger the area disposed in the passage region S secured by the lower side concave portion 6a, the more preferable. However, an overlap (overlaying) of a part of the slit 7b on the inner seal portion 13 causes a possibility of impeding formation of the inner seal portion 13. It is thus preferable that the distance L3 be a distance at least "0", that is, a distance that is not minus (negative).

Likewise, also about the blood flows F1 (see FIG. 5) from the diffusing opening 7c toward the passage region S, in view of stably maintaining the flow rate of flows F1, it is preferable that the distance L4 from the end 7g of the diffusing opening 2c to the end 13g of the lateral side portion 13c nearer to the diffusing opening 7c be smaller (shorter). That is, in the area of the diffusing opening 7c (see FIG. 4), the larger the area disposed in the passage region S secured by the lateral side concave portions 6c, the more preferable. However, an overlap (overlaying) of a part of the diffusing opening 7c on the inner seal portion 13 causes a possibility of impeding formation of the inner seal portion 13. It is thus preferable that the distance L4 be a distance at least "0", that is, a distance that is not minus (negative). In this embodiment, the distances L3 and L4 are formed to be equal to each other, but may be different from each other.

The distance L3 and the distance L4 range from 0 to 4 mm, preferably 0 to 3 mm, more preferably 0 to 2 mm, and further preferably, 0 to 1.5 mm. To improve the flow characteristics, 0 mm is preferred. However, in a process with a low accuracy of alignment during filter formation, a distance larger than 0 mm can be adopted in order to reduce malfunction.

Typically, the thickness t of the flow path securing sheet 7 can be substantially the same as that of the flexible container 3. The larger the thickness t of the flow path securing sheet 7 is, the larger the flow path is secured even with the same slit width L2 of the slit 7b. Thus, concern of blockage due to bending of the outlet-side container 11 is reduced. On the other hand, the larger the thickness t of the flow path securing sheet 7 is, the more the amount of loss of the blood preparation qualitatively tends to increase owing to increase of the space in the slit 7b. Consequently, it is preferred that the thickness t of the flow path securing sheet 7 be 0.1 to 3.5 mm, preferably, 0.1 to 3.0 mm, more preferably, 0.2 to 2.5 mm, and further preferably, 0.5 to 2.0 mm, and 0.5 to 1.5 mm. Preferably, the thickness t of the flow path securing sheet is designed in consideration of presence or absence of a post-filter layer.

Next, materials and shapes of elements used for the blood processing filter 1A are described. As described above, the flexible container 3 is formed of the inlet-side container 9 and the outlet-side container 11. Any material commercially available as a sheet or a film can be utilized as a flexible resin to be used for the flexible container 3. Examples of preferable materials include thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate and the like. Since it can be considered that the material will be in contact with blood, preferable materials include soft polyvinyl chloride, polyurethane, and polyolefin that are used as the material of medical products such as blood bags, as well as thermoplastic elastomers containing these materials as main components, and more preferably, soft polyvinyl chloride.

In particular, a methods of manufacturing erythrocyte preparations often includes a step of centrifugation for separating blood components. However, in view of not damaging another member, such as a blood bag, during storage into the centrifuge, it is preferred to use the blood processing filter 1A that includes the flexible container 3. Because of excellent steam permeability, the blood processing filter 1A that includes the flexible container 3 is desired for its excellence in sterilization. Furthermore, the blood processing filter 1A that includes the flexible container 3 is economically excellent in comparison with a filter in a hard container. Furthermore, for example, a container described in Japanese Unexamined Patent Publication No. H7-267871 or a container described in International Publication No. WO 95/017236 can also be used as the flexible container 3.

The filter element 5 is manufactured using a filter material made of a fibrous integrated body such as nonwoven fabric or woven fabric or of a porous body such as sponge. The filter element 5 according to this embodiment may be coated with a hydrophilic polymer to facilitate the filter material being wet with blood. Furthermore, to facilitate attachment of leukocytes to the filter element 5 in the case of using the blood processing filter 1A to remove leukocytes from blood, a filter material coated with a polymer may be used.

In the filter element 5 (see FIG. 1), for example, the prefilter layer 51, the main filter layer 52, and the post-filter layer 53 are stacked in this order from the element nearer to the inlet-side container 9. The prefilter layer 51 is made of nonwoven fabric with an average fiber diameter ranging from several to several tens of micrometers, and has a function of capturing microaggregates in blood. More specifically, the prefilter layer 51 can be formed by stacking one or more (e.g., two to six) sheets of nonwoven fabric with an air permeability of 180 to 300 ($cc/cm^2/sec.$) and a thickness of 0.2 to 2.0 (mm). Here, it is preferred that the air permeability of the nonwoven fabric be 200 to 280 ($cc/cm^2/sec.$), and more preferred that the permeability be 220 to 260 ($cc/cm^2/sec.$). Furthermore, it is preferred that the thickness of nonwoven fabric be 0.5 to 1.5 (mm), and more preferred that the thickness be 0.6 to 1.2 (mm). Note that in the case of adopting relatively thin nonwoven fabric, a large number of sheets thereof are stacked to form it. In the case of adopting relatively thick nonwoven fabric, only a small number thereof are sufficient to be stacked to form it.

The main filter layer 52 is made of nonwoven fabric having an average fiber diameter smaller than the prefilter layer 51, and has a function of mainly removing leukocytes and thrombocytes. More specifically, the main filter layer 52 can be formed by stacking several sheets of nonwoven fabric each having an air permeability of 6.0 to 9.0 (cc/cm$^2$/sec.) and a thickness of 0.1 to 1.0 (mm). However, in the case of adopting relatively thin nonwoven fabric, the layer is formed by stacking a large number of sheets. In the case of adopting a relatively thick nonwoven fabric, a small number of sheets are sufficient to be stacked to form it.

The post-filter layer 53 is made of, for example, nonwoven fabric with an average fiber diameter ranging from several to several tens of micrometers, and is a filter layer formed by stacking one or more (e.g., two to six) sheets of nonwoven fabric each having an air permeability of 180 to 300 cc/cm$^2$/sec. and a thickness of 0.2 to 2.0 mm. Here, it is preferred that the air permeability of the nonwoven fabric be 200 to 280 (cc/cm$^2$/sec.), and more preferred that the permeability be 220 to 260 (cc/cm$^2$/sec.). Furthermore, it is preferred that the thickness of nonwoven fabric be 0.5 to 1.5 (mm), and more preferred that the thickness be 0.6 to 1.2 (mm). Note that in the case of adopting relatively thin nonwoven fabric, a large number of sheets thereof are stacked to form it. In the case of adopting relatively thick nonwoven fabric, only a small number thereof are sufficient to be stacked to form it. The post-filter layer 53 is disposed on the flow path securing sheet 7 side, and has a function of securing the flow toward the outlet port 11a. The prefilter layer 51 and the post-filter layer 53 may be the same. Note that the filter element 5 may be a single filter layer.

Since the blood processing filter 1A according to this embodiment includes the post-filter layer 53, this filter can reduce the remaining amount of blood preparation in the blood processing filter 1A while forming the blood flow path having an appropriate air permeability resistance. As a result, it is further advantageous to enjoy effects of increasing the collecting rate while maintaining the flow rate. This embodiment does not include many ribs but includes only two ribs 7a around the outlet port 11a, thus allowing use of the flow path securing sheet 7 where wide diffusing openings 7c are formed besides the slit 7b. In the case of using the flow path securing sheet 7 according to this embodiment, in particular, to maintain the flow rate, the post-filter layer 53 is effectively provided. The importance of stacking the post-filter layer 53 is further improved.

The flow path securing sheet 7 can be manufactured using the same material as that of the flexible container 3, and the slit portions 7b and the diffusing openings 7c can be appropriately manufactured by a punching process or another method. As with the flow path securing sheet 7, the frame sheet 10 can be manufactured using the same material as that of the flexible container 3, and the first opening 10b and the second opening 10c can be appropriately manufactured by a punching process or another method.

Figure 10:
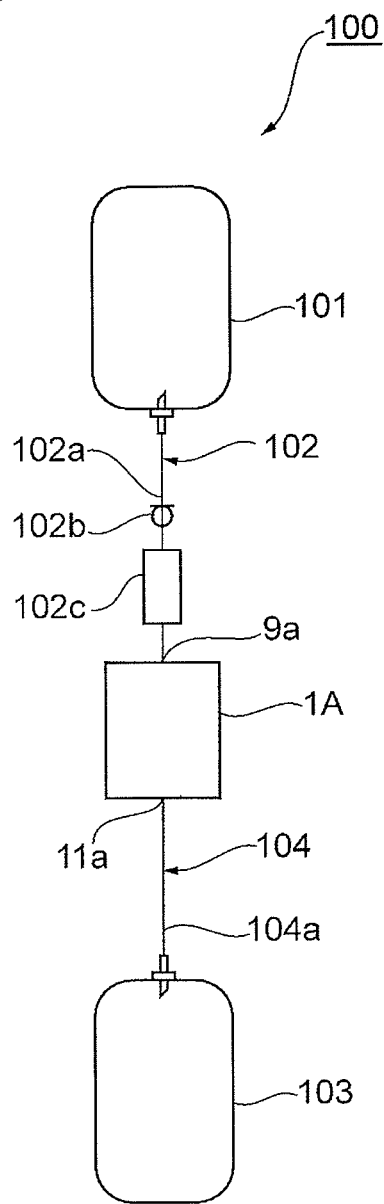
FIG. 10 is a front view that schematically shows a blood processing system that includes a blood processing filter.

Next, a blood processing system 100 configured by including the blood processing filter 1A according to the first embodiment is described with reference to FIG. 10. FIG. 10 is a front view that schematically shows the blood processing system.

The blood processing filter 1A can be used for filtering using gravity. For example, the blood processing system 100 to which the blood processing filter 1A is applied includes a reservoir bag 101 storing blood having been collected, the blood processing filter 1A, and a recovery bag 103 for accumulating blood having been filtered. The reservoir bag 101 and the inlet port 9a of the blood processing filter 1A are connected to each other by a tube 102a, such as a blood tube. The recovery bag 103 and the outlet port 11a of the blood processing filter 1A are connected to each other by a tube 104a, such as a blood tube. Furthermore, opening/closing means 102b such as a roller clamp that opens and closes a flow path, and a chamber 102c and the like are mounted in the tube 102a on the upstream side. The inlet-side circuit 102 is formed of the tube 102a, the opening/closing means 102b, and the chamber 102c and the like. The outlet-side circuit 104 on the downstream side is formed of the tube 104a and the like.

The reservoir bag 101 storing blood having been collected is placed at a position that is 30 to 70 cm higher than the blood processing filter 1A. The recovery bag 103 for accumulating blood having been filtered is arranged at a position that is approximately 50 to 120 cm lower than the blood processing filter 1A. The total head is 150 cm. A blood filtering process is performed by opening the flow path of the blood processing system 100. While a filtering process is performed (at a time of use), a negative pressure arises on the outlet side of the flexible container 3 of the blood processing filter 1A, and the outlet-side container 11 deforms and is prone to come to the filter element 5. However, as shown in FIG. 5, the concave portion 6 is formed on the outlet side of the filter element 5. Consequently, the passage region S serving as the blood flow path is formed between the filter element 5 and the outlet-side container 11. Furthermore, since a part of the slit portions 7b of the flow path securing sheet 7 is disposed in the passage region S, and the passage region S communicates with to the outlet port 11a, the blood flow path allowing communication from the slit portions 7b to the outlet port 11a is stably maintained without being blocked.

Next, the operations and advantageous effects of the blood processing filter 1A according to this embodiment are described. According to the blood processing filter 1A, even if a dual force caused by a positive pressure on the inlet side and a negative pressure on the outlet side is applied during filtration, the flow of blood is ensured between the slit 7b of the flow path securing sheet 7 and the outlet port 11a. Consequently, impediment of flows and reduction in filtering performance due to close contact between the outlet-side container 11 of the blood processing filter 1A and the filter element 5 and the like are avoided, which is advantageous to effectively utilize the entire filter element 5, and can compatibly achieve a high filtering flow rate and a high filtering performance.

Particularly, according to the blood processing filter 1A according to this embodiment, at least a part of the slit 7b and the diffusing openings 7c that are formed in the flow path securing sheet 7 is disposed to communicate with the concave portion 6, and disposed in the passage region S formed of the concave portion 6 in the state of allowing blood to flow. Consequently, all the slit 7b and the two diffusing openings 7c are caused to communicate with each other via the passage region S, and can prevent reduction in filtering performance due to blockage of the blood flow path. Since blood having flowed from the diffusing opening 7c flows into the passage region S and diffuses, no blockage of flows such as concentration to the outlet port 11a occurs. Thus, the blood flow becomes uniform in the outlet-side container 11. Consequently, the entire filter element 5 is effectively utilized, which achieves a high flow rate and high filtering performance at the same time.

Furthermore, in the blood processing filter 1A according to this embodiment, since at least a part of the outlet opening 11c of the outlet port 11a is disposed so as to be overlaid on the slit 7b in a plan view, blood having processed by the filter element 5 can be effectively discharged to the outside of the blood processing filter 1A, and at the same time the possibility of blockage of the outlet opening 11c due to the filter element 5 can be avoided. The outlet port 11a may be disposed so as to overlay on the passage region S in a plan view.

Furthermore, in the blood processing filter 1A according to this embodiment, the outlet-side container 11 is not included in the inner seal portion 13. Consequently, the flow can be prevented from being impaired by the filter element 5 in proximity to the inner seal portion 13 being sandwiched by the flexible container 3. In addition thereto, the passage region S is formed of the concave portion 6 corresponding to the inner seal portion 13, and the passage region S can be utilized as a blood flow path. Thus, in the conventional blood processing filter, for example, the blood processing filter 1E of a first comparative mode (see FIG. 14), there is a tendency that the filter material at the peripheral portion of the filter element 5 in proximity to the inner seal portion 113 is difficult to cause blood to flow, while the blood processing filter 1A according to this embodiment can effectively utilize the filter element 5 in proximity to the inner seal portion 13.

Figure 14:
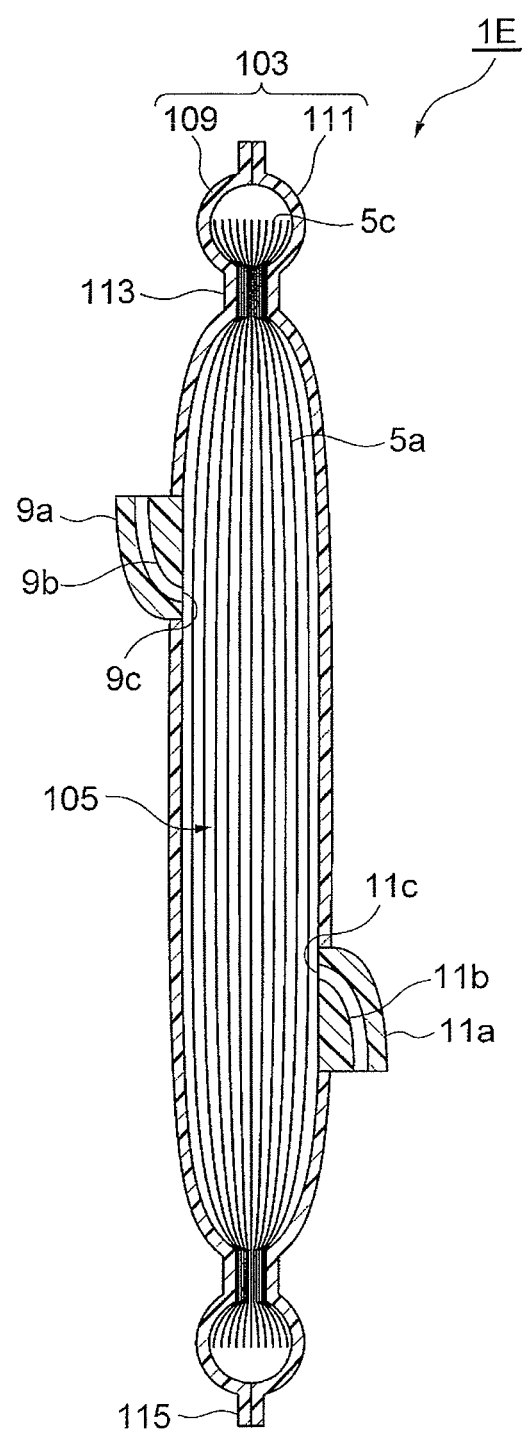
FIG. 14 is a longitudinal sectional view of a blood processing filter according to a first comparative mode.

Note that as shown in FIG. 14, the blood processing filter 1E is different from the blood processing filter 1A according to this embodiment in that the filter 1E does not include the flow path securing sheet 7 or the frame sheet 10, the inlet-side container 109, the filter element 105 and the outlet-side container 111 are stacked, and the inner seal portion 113 and the outside seal portion 115 are formed. For the sake of convenience, the other elements of the blood processing filter 1E common to those of the blood processing filter 1A are assigned the same symbols.

Furthermore, in the blood processing filter 1A according to this embodiment, the flow path securing sheet 7 includes diffusing openings 7c each having a large opening area. Consequently, the blood preparation is stagnant-proof, which can improve the blood preparation collecting rate.

In the blood processing filter 1A of this embodiment, the flow path securing sheet 7 and the frame sheet 10 have the same shape and are rotationally symmetric, and the outlet-side container 11 and the inlet-side container 9 have the same shape and are rotationally symmetric. Furthermore, in the filter element 5, the prefilter layer 51 and the post-filter layer 53 have the same symmetric shape. Consequently, the outlet-side container 11 and the inlet-side container 9 can be used in an inverted manner. This allows use without consideration of the outlet and inlet. Furthermore, the number of types of component materials is reduced, thereby allowing the manufacturing process to be simplified.

The flow path securing sheet 7 of the blood processing filter 1A of this embodiment has a smaller number of ribs 7a than blood processing filter 1F of a second comparative mode (see FIG. 15), and thus has a simple shape. The force required to punch the flow path securing sheet 7 is proportional to the total sum of the lines to be punched. Consequently, according to the blood processing filter 1A, only small force is required to punch the flow path securing sheet 7, thereby facilitating processing. Furthermore, the deterioration of a punching blade and the like are reduced, and occurrence of cutting burrs is reduced. Moreover, in the blood processing filter 1F of the second comparative mode, the flow path securing sheet 7 is provided with many (at least three) ribs 7k, and the swarf occurring during cutting is fine and the number of pieces thereof is large. Consequently, the swarf is prone to be jammed in the flow path hole 7h. However, in the blood processing filter 1A of this embodiment, the swarf occurring during cutting is large and the number of pieces is small. Consequently, it is difficult to cause such a phenomenon.

Note that the blood processing filter 1F according to the second comparative mode includes not only the ribs 7k corresponding to the ribs 7a of this embodiment but also a plurality of ribs 7k having the same width L6 as the ribs 7k, and further includes a plurality of slit-shaped flow path holes 7h in the inner seal portion 130. The blood processing filter 1F is different from the blood processing filter 1A of this embodiment in that the number of ribs 7k of the flow path securing sheet 107 is different. For the sake of convenience, the other elements of the blood processing filter 1F common to those of the blood processing filter 1A are assigned the same symbols.

The above description is summarized. That is, in comparison between the case of manufacturing the flow path securing sheet 107 including many opening holes in the blood processing filter 1F and the case of manufacturing the flow path securing sheet 7 including the slit 7b and the diffusing openings 7c in the blood processing filter 1A, the blood processing filter 1A requires a smaller force for punching, thereby facilitating manufacture and achieving economy. Thus, the filter 1A is preferable. In the case of the blood processing filter 1F where many opening holes have been punched out, swarf tends to be caused. On the contrary, in the case of the blood processing filter 1A, the number of opening holes to be punched is small. Consequently, swarf is resistant to occurring, which reduces defectives. Thus, the filter 1A is preferable.

In the blood processing filter 1A of this embodiment, the filter element 5 includes the post-filter layer 53. In the blood processing filter 1A, the opening area of the diffusing openings 7c is large. Consequently, the filter element 5 corresponding to this portion is prone to adhere to the outlet-side container 11. However, presence of the post-filter layer 53 allows the blood flow to be secured. On the contrary, the blood processing filter 1E of the first comparative mode does not include the passage region S made of the concave portion 6 and concentrates the blood flow in the outlet port 11a. Consequently, the amount of post-filter layer 53 is required to be increased, which in turn increases the amount of loss of the blood preparation.

Although the present invention has thus been described with reference to the one embodiment, the present invention is not limited to the above embodiment. For example, in the embodiment, the example is shown where the pair of ribs 7a are made up of lines continuous from the lower side portion 13a to the upper side portion 13b, and the slit 7b opens continuously from the lower side portion 13a to the upper side portion 13b. However, any mode can be adopted where the ribs are disposed opposite to each other with the outlet port interposed therebetween, the slit communicates with the concave portion formed of the communication portion. Various shapes may be adopted.

Figure 11:
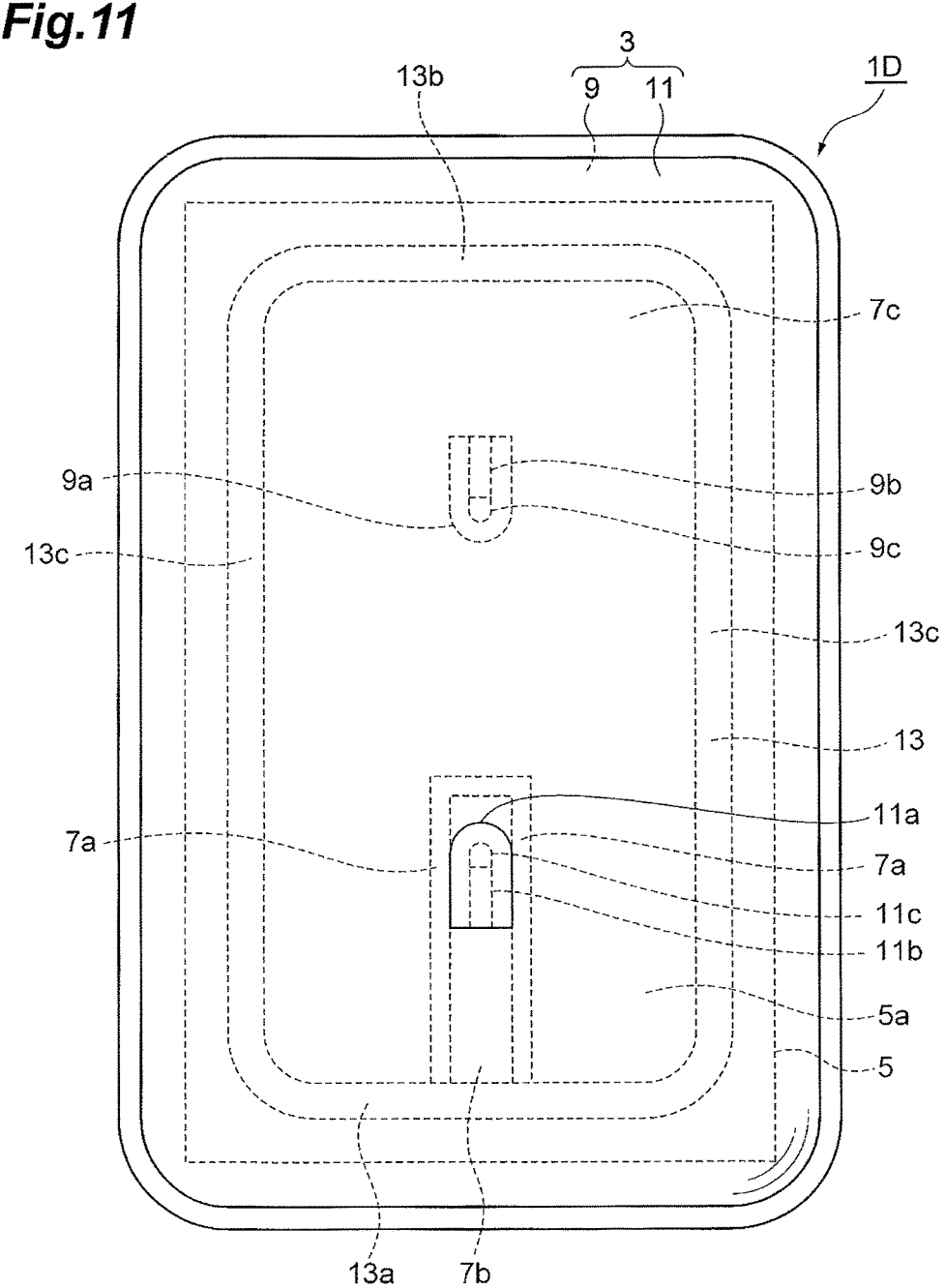
FIG. 11 is a plan view of the blood processing filter according to a variational example.

FIG. 11 is a plan view of a blood processing filter 1D according to a variational example. As shown in FIG. 11, the pair of ribs 7a are not continuous to the upper side portion 13b, and have the distal ends connected to each other so as to surround the outlet port 11a. In this case, portions of the diffusing openings 7c that are disposed nearer to the upper side portion 13b than the ribs 7a are continuous to each other between the pair of lateral side portions 13c. According to the blood processing filter 1D, to an extent by which the ribs 7a are shortened, the blood-stagnant portion is reduced, thereby allowing the amount of blood loss to be reduced. In this embodiment and variational examples thereof, for example, the pair of ribs 7a may be a straight line, a bent line, a curve, or any combination thereof.

In the above embodiment, the example where the diffusing openings 7c are made up of two portions having the same shape, and open continuously from the lower side portion 13a to the upper side portion 13b. Alternatively, the diffusing openings 7c may be any of various shapes only if they have forms communicating with the lateral side concave portions 6c formed of the lateral side portions 13c. For example, the two diffusing openings 7c may have different sizes. Alternatively, the flow path securing sheet 7 may include lateral ribs continuous from the ribs 7a to the lateral side portions 13c, and the diffusing openings 7c are a plurality, which is at least three, of portions.

Use of the blood processing filter 1A according to this embodiment can achieve high average processing speed. More specifically, when the following examination for performance evaluation is performed, a result where the average processing speed (g/min.) is at least 12.0 g/min.

In this examination, for example, the aforementioned blood processing system 100 is used to evaluate the performance of the blood processing filter 1A. More specifically, liquid to be processed is used instead of blood, 300 g of the liquid to be processed is injected into the reservoir bag (liquid reservoir bag before filtration) 101, and subsequently, 15 mL of air is injected. This liquid to be processed is polyvinylpyrrolidone (weight-average molecular weight of 360000) aqueous solution (K90/Wako Pure Chemical Industries, Ltd.) prepared to have a viscosity of 17 mPa·s and pH 3.8 at a temperature of 25° C.

In a state where the recovery bag (liquid recovery bag) 103 is placed on the recovery stage, the reservoir bag 101 is fixed at a predetermined height. More specifically, the total head that is a total of an upstream-side head from the reservoir bag 101 to the inlet port 9a (inlet) of the blood processing filter 1A, a head between the inlet port 9a and the outlet port (outlet) 11a of the blood processing filter 1A, and a downstream-side head from the outlet port (outlet) 11a of the blood processing filter 1A to the recovery bag 103, is fixed to 150 cm.

After the placement of the blood processing system 100 is finished, the average processing speed is calculated from the amount of recovery and the total processing time in the case where the liquid to be processed is caused to flow using gravity at room temperature (22° C.±2° C.). Thus, a result with at least an average processing speed (g/min.) of 12.0 g/min. can be obtained. Preferably, the average processing speed (g/min.) is at least 15.0 g/min., more preferably, at least 17.0 g/min.

The main factor to obtain the result with the average processing speed (g/min.) of at least 12.0 g/min. is considered the relationship between the slit 7b and the diffusing openings 7c of the flow path securing sheet 7. More specifically, in the blood processing filter 1A according to this embodiment, the post-filter layer 53 is provided so as to be overlaid on the flow path securing sheet 7. Furthermore, the outlet port 11a is disposed so as to be overlaid on the slit 7b of the flow path securing sheet 7. The slit 7b is an elongated opening, and disposed so as to be overlaid on the outlet port 11a. Consequently, the main flow of the liquid to be processed in a region overlaid on the slit 7b is a flow in a direction parallel to the slit 7b and toward the outlet port 11a (outlet opening 11c). On the other hand, the diffusing openings 7c are outside of the pair of ribs 7a, continuously open from the ribs 7a to the lateral side portions 13c, and communicates with the concave portion 6 formed of the lateral side portions 13c. As a result, the flow of the liquid to be processed in the post-filter layer 53 within the region overlaid on the diffusing openings 7c is not unidirectional but is a flow diffusing toward the concave portion 6.

That is, in the region overlaid on the diffusing opening 7c, an action that radially flows from the center of the rib 7a and its proximity to the nearest concave portion 6 is integrated with an action that tends to flow downward when being affected by gravity to form a flow diffusing toward the concave portion 6. Here, there is a tendency that the higher the flow rate of blood is, the relatively smaller the effects by gravity becomes to thereby form a flow like a radial flow. In the case where the blood processing filter 1A is horizontally placed, substantially all of the actions of gravity can be ignored. Consequently, the flow becomes that like a radial flow. This diffusing flow is achieved by the structure of the blood processing filter 1A. On the other hand, in the blood processing filter 1E of the first comparative mode, the flow does not diffuse but becomes a flow concentrating to the outlet port 11a (outlet opening 11c). That is, the blood processing filter 1A according to this embodiment can effectively utilize the filter element without waste as a result of the diffusing flow in the region overlaid on the diffusing opening 7c. Consequently, it can be considered that the average processing speed (g/min.) of at least 12.0 g/min. has been achieved.

Furthermore, through use of the blood processing filter 1A according to this embodiment, the remaining amount of blood (amount of loss) in the blood processing filter 1A after completion of the blood processing can be reduced. More specifically, when the following examination for performance evaluation is performed, the following result where the remaining amount of liquid to be processed in the blood processing filter 1A after filtration is 30 g or less can be at least achieved.

Likewise, as described above, in this examination the blood processing system 100 is used to evaluate the performance of the blood processing filter 1A. Furthermore, up to provision of the blood processing system 100, the process is the same as that of the aforementioned examination. The total head that is a total of an upstream-side head from the reservoir bag 101 storing the liquid to be processed and air of 15 mL to the inlet port 9a (inlet) of the blood processing filter 1A, a head between the inlet port 9a and the outlet port (outlet) 11a of the blood processing filter 1A, and a downstream-side head from the outlet port (outlet) 11a of the blood processing filter 1A to the recovery bag 103, is fixed to 150 cm.

After the placement of the blood processing system 100 is finished, the remaining amount of liquid to be processed in the blood processing filter 1A after filtration is measured in the case where the liquid to be processed is caused to flow using gravity at room temperature (27° C.). Consequently, a result where the remaining amount of 30.0 g or less can be at least achieved. Preferably, the remaining amount is 28 g or less, and further preferably, 26 g or less.

The main factor of obtaining the result of the remaining amount of 30 g or less is provision of the post-filter layer 53. Furthermore, to reduce the remaining amount of liquid, the effect of the number of ribs 7a of the flow path securing sheet 7 disposed on the outlet side is considered great.

Next, the characteristics of a blood processing method using the blood processing filter 1A are described. According to the aforementioned characteristics of the blood processing filter 1A, unbiased use of blood flowing uniformly through the filter element 5 is achieved. That is, as shown in FIG. 8, when L3 has a sufficiently small value, the passage region S formed of the concave portion 6 and the flow path formed of the diffusing openings 7c and the pair of ribs 7a communicate with each other, thereby allowing the flows F1, the flows F2 and the flows F3 in FIG. 5 to be achieved, which achieves uniform use of the filter element 5 as shown in FIG. 7. Note that the flows F1 in FIG. 5 are flows flowing from the ribs 7a toward the lateral side portions 13c, the lower side portion 13a or the upper side portion 13b in the regions of the diffusing openings 7c. The flows F2 are flows flowing through the passage region S. The flows F3 are flows flowing through the flow path formed of the ribs 7a.

At this time, the flows F1 in FIG. 5 forms a flow diffusing that not only pass the gap formed between the outlet-side container 11 and the filter element 5 but also flow through the post-filter layer 53 having a lower liquid permeable resistance than the main filter layer 52 toward the passage region S. It is herein preferable that the flows F1 have directions other than the directions parallel to the ribs 7a. The flows F2 flow through the annular passage region S, form flows toward a coupling portion between the passage region S and the flow path formed of the slit 7b inside of the pair of ribs 7a. The flows F3 form flows flowing through the flow path formed of the pair of ribs 7a (the flow path in the slit 7b) toward the outlet port 11a.

In the blood processing method according to this embodiment, the flows as described above are formed, thereby allowing a higher average processing speed (g/min.) to be achieved even if the same filter element 5 is adopted. The high average processing speed (g/min.) can be achieved through more uniform use of the filter element 5. As a result, a high removal ratio can also be achieved. For example, in the case of using the blood processing filter 1A according to this embodiment for the sake of removing leukocytes, this is advantageous to improve the leukocyte removal ratio, and can achieve a higher leukocyte removal ratio than the conventional blood processing filter and leukocyte removing method.

In the blood processing filter 1A according to this embodiment, the pair of ribs 7a are formed in the flow path securing sheet 7 to form the slit 7b and the diffusing openings 7c, and the post-filter layer 53 is disposed in the filter element 5 on the side nearer to the flow path securing sheet 7, thereby allowing the entire surface of the filter element 5 and the outlet port 11a to be coupled to each other through the passage region S. In particular, only one pair of ribs 7a are provided, thereby allowing a small amount of reduced loss (g) to be achieved even in the case where the same filter element 5 is adopted. In order to achieve not only the high average processing speed and filtering performance (leukocyte removal ratio) but also the high amount of recovery (small amount of loss), it is significantly effective to control the provision and physical properties of the post-filter, and the design of the flow path securing sheet 7 (in particular, the value of L3, thickness, and the sizes of slit and diffusing openings).

Furthermore, it is preferred that the blood processing filter 1A of this embodiment be used in the blood processing method that performs retro-priming. The retro-priming is a preprocessing method of blood processing, and is an operation that preliminarily causes a stock solution to pass through the blood processing filter in a direction reversed to that during blood processing, makes the blood processing filter wet, and preliminarily remove air in the system. For example, it can be considered that the stock solution in the recovery bag is caused to pass through the blood processing filter and is conveyed to the reservoir bag to dilute the blood preparation in the reservoir bag, and subsequently performs a normal blood processing. If the blood processing is performed with air left remained in the blood processing filter, the filtering area of the filter element cannot be effectively utilized. Consequently, a lopsided flow occurs, which leads to reduction in flow rate and filtering performance. By performing retro-priming, the air in the blood processing filter can be removed before blood processing. Consequently, the flow rate is improved, which can maintain the filtering performance. After blood processing, by air in the reservoir bag, the blood preparation remaining in the tube connecting the blood bag and the blood processing filter or in the filter is squeezed, which can improve the collecting rate. The blood processing filter 1A of this embodiment compatibly achieves the high processing speed and the collecting rate. Through its use for the blood processing method that performs retro-priming, the performance can be exerted.

It is preferred that the blood processing filter 1A of this embodiment be used for the blood processing method for performing blood processing that connect this filter to the blood preparation in a top and bottom system. When whole blood where donated blood and anticoagulant are mixed is centrifuged, a blood plasma layer with a small specific gravity is formed in an upper part, a packed erythrocyte layer made up of erythrocytes with a large specific gravity is formed in lower part, and a buffy coat layer made up mainly of thrombocytes and leukocytes is fainted therebetween. Then, after the centrifuging, the blood plasma is transferred from an upper outlet of the blood bag, the packed erythrocytes are transferred from a lower outlet, to the respective different containers, and only the buffy coat is remained. The system using the upper outlet and the lower outlet is the top and bottom system. The packed erythrocytes transferred from the lower outlet have a high hematocrit value. Consequently, filtration thereof as they are is not preferable in view of flow characteristics. With a blood preparation with a high hematocrit value, blood is prone to remain in the system, and the collecting rate is prone to be reduced. It is preferred that the blood processing filter 1A of this embodiment be used to be connected to the blood preparation in the top and bottom system, and used to process the packed erythrocyte preparation. In order to reduce the hematocrit value of packed erythrocytes, mixing with erythrocyte preservation solution before filtration is effective. With the retro-priming performed here, transfer of air in the system to the pre-filtration blood bag is performed in addition to mixing to prepare for a collection step thereafter. Thus, humidification of the filter can be achieved at the same time. As described above, it is preferred that the blood processing filter 1A of this embodiment be used to be connected to the blood preparation in the top and bottom system, and used for blood cell processing that performs retro-priming.

Figure 12:
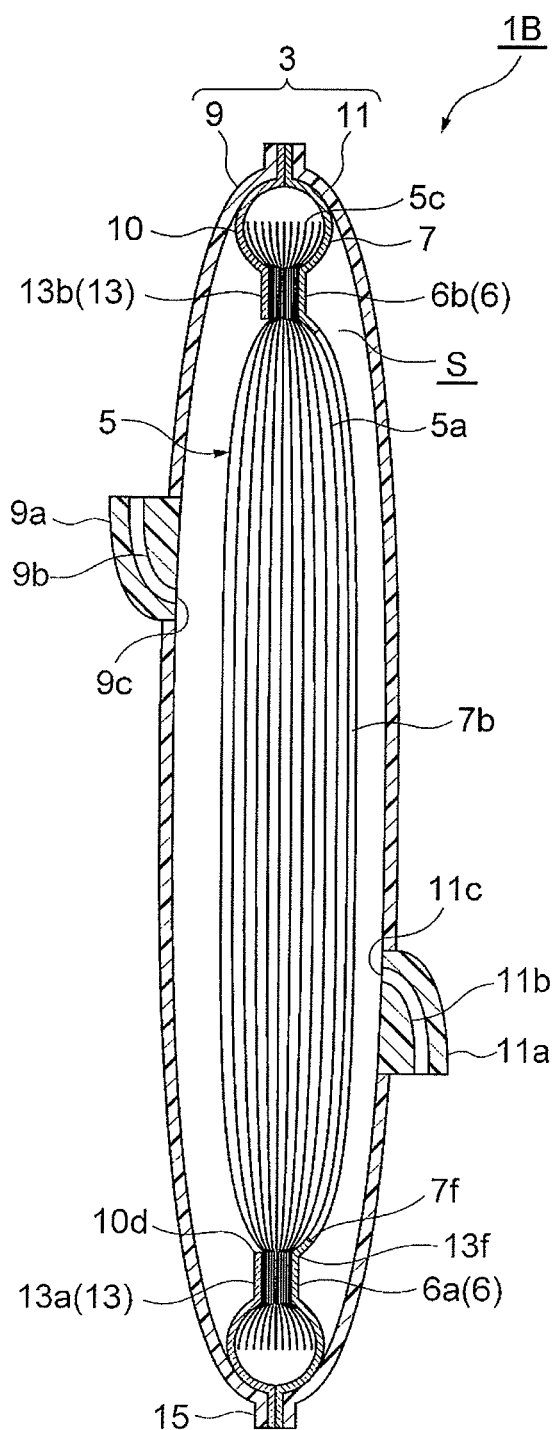
FIG. 12 is a longitudinal sectional view of a blood processing filter according to a second embodiment.

Next, referring to FIG. 12, a blood processing filter 1B according to a second embodiment is described. The blood processing filter 1B includes the substantially same elements and structures as the blood processing filter 1A. Hence, the same elements and structures are assigned the same reference symbols and a detailed description thereof is omitted, and the following description centers on different elements and structures.

As shown in FIG. 12, the blood processing filter 1B is different from the blood processing filter 1A in that the frame sheet 10 includes no rib 10a. All the first opening 10b and the second openings 10c are connected to each other to form one opening 10d. That is, in the frame sheet 10, the single opening 10d is provided in a form where the entire inner portion surrounded by the inner seal portion 13 is cut out.

According to the blood processing filter 1B, as with the blood processing filter 1A, even if a dual force is applied by means of the positive pressure on the inlet side and the negative pressure on the outlet side during filtration, through the passage region S formed of the concave portion 6, the outlet port 11a can communicate with the slit 7b and the diffusing openings 7c of the flow path securing sheet 7. Consequently, impediment of blood flows due to close contact between the outlet-side container 11 and the filter element 5, and reduction in filtering performance can be avoided.

According to the blood processing filter 1B, since the frame sheet 10 does not include the ribs 10a, blood stagnancy at this portion is removed, which can reduce the amount of loss of the blood preparation.

Figure 13:
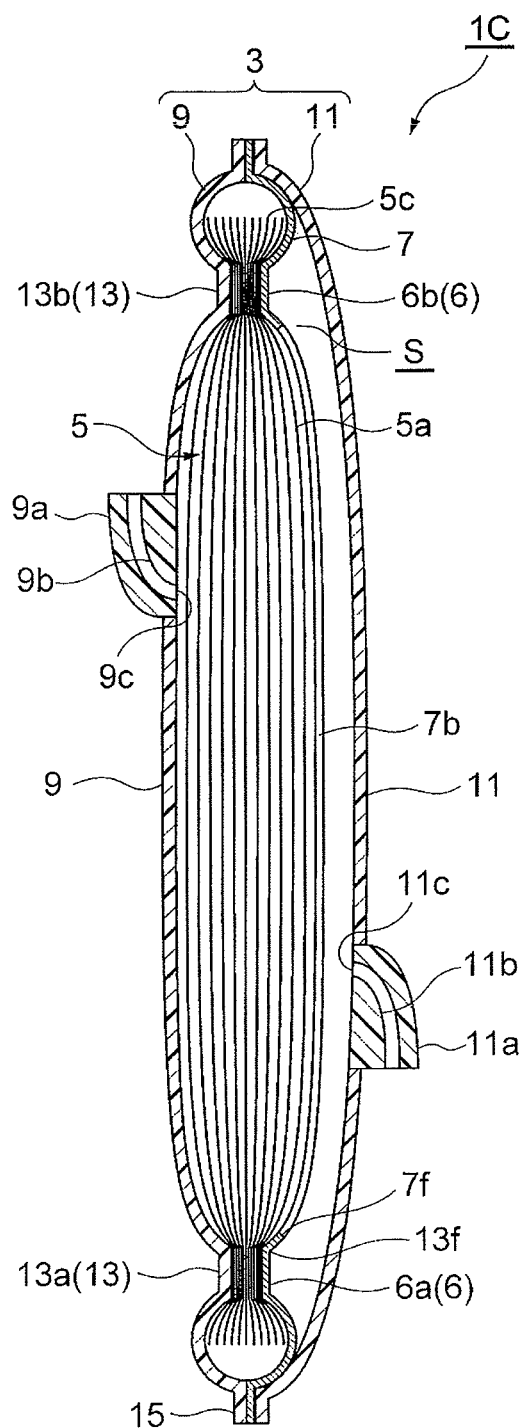
FIG. 13 is a longitudinal sectional view of a blood processing filter according to a third embodiment.

Next, referring to FIG. 13, a blood processing filter 1C according to a third embodiment is described. The blood processing filter 1C includes the substantially same elements and structures as the blood processing filter 1A. Hence, the same elements and structures are assigned the same reference symbols and a detailed description thereof is omitted, and the following description centers on different elements and structures.

As shown in FIG. 13, the blood processing filter 1C is different from the blood processing filter 1A in that the filter 1C does not include the frame sheet 10, and the inner seal portion 13 is in close contact with and sandwiches the filter element 5 between the inlet-side container 9 and the flow path securing sheet 7.

According to the blood processing filter 1C, as with the blood processing filter 1A, even if a dual force is applied by means of the positive pressure on the inlet side and the negative pressure on the outlet side during filtration, through the passage region S formed of the concave portion 6, the outlet port 11a can communicate with the slit 7b of the flow path securing sheet 7 and the diffusing openings 7c. Consequently, impediment of blood flows due to close contact between the outlet-side container 11 and the filter element 5, and reduction in filtering performance can be avoided.

Furthermore, since the frame sheet 10 is not included, the cost therefor is reduced accordingly. Furthermore, since the inlet-side container 9 is sealed at the inner seal portion 13, the space of the filter element 5 on the inlet side is difficult to swell owing to the positive pressure during filtration.

EXAMPLES

The present invention will now be described in further detail below by way of Examples. However, the present invention should not be limited by Examples.

Example

Example adopted a filter corresponding to the blood processing filter 1A (see FIG. 3) according to the aforementioned first embodiment. More specifically, a filter including an inlet-side container (inlet-side flexible container), an outlet-side container (outlet-side flexible container), a filter element, a frame sheet, and a flow path securing sheet was used, and an inlet port thereof was connected to a pre-filtration liquid reservoir bag via an inlet-side circuit having a length of 50 cm. An outlet port of the filter was connected to a post-filtration liquid recovery bag via an outlet-side circuit having a length of 100 cm. A tube made of soft polyvinyl chloride having an internal diameter of 2.9 mm and an external diameter of 4.2 mm was used for the inlet-side circuit and the outlet-side circuit.

In preparing the filter, an effective filtering portion was formed in a rectangular shape in which an inner side of an inside seal part (first seal part) had a longitudinal dimension of 74 cm and a lateral dimension of 57 cm, a corner portion was formed as a curve, and an effective filtration area of $42 \times 10^{-4}$ (m$^2$) was provided. As the filter element, four sheets of polyester nonwoven fabric having an air permeability of 237.3 (cc/cm$^2$/sec.) and a thickness of 0.2 mm, one sheet of polyester nonwoven fabric having an air permeability of 8.4 (cc/cm$^2$/sec.) and a thickness of 0.4 mm, 32 sheets of polyester nonwoven fabric having an air permeability of 7.7 (cc/cm$^2$/sec.) and a thickness of 0.20 mm, one sheet of polyester nonwoven fabric having an air permeability of 8.4 (cc/cm$^2$/sec.) and a thickness of 0.4 mm, and four sheets of polyester nonwoven fabric having an air permeability of 237.3 (cc/cm$^2$/sec.) and a thickness of 0.2 mm were stacked in this order from an inlet to an outlet at the time of filtering blood, and used. Note that the air permeability was measured by a method based on Japanese Industrial Standard JIS L-1096, 6.27.1A.

The same flexible sheet with a thickness of 0.4 mm was used for the inlet-side container, the outlet-side container, the frame sheet, and the flow path securing sheet.

The filter element was sandwiched and sealed at the same time by the frame sheet and the flow path securing sheet, thus forming the inner seal portion. Next, the filter element sealed at the inner seal portion by the frame sheet and the flow path securing sheet was sandwiched by the inlet-side container and the outlet-side container, thus sealing the inlet-side container, the frame sheet, the flow path securing sheet, and the outlet-side container at the same time, which formed the outside seal portion. In each of the frame sheet and the flow path securing sheet, in the same manner, two ribs having a width of 3 mm and an interval of 4 mm were fabricated in the vertical direction and bilaterally symmetrically disposed at portions inside of the inner seal portion. Portions of the frame sheet and the flow path securing sheet inside of the inner seal portion served as flow path holes except the ribs. That is, the frame sheet is in a state of having the first opening and two second openings as flow path holes, and the flow path securing sheet was in a state of having the slit and two diffusing openings as flow path holes.

The inlet port was sealed and assembled such that during being sealed at the inlet-side container, an inlet opening for allowing blood to flow from the inlet port into the flexible container at a position 2.4 cm below an end of the effective filtering portion of the upper side portion of the inner seal portion and at the center between the pair of lateral side portions of the inner seal portion. Furthermore, an outlet port was sealed and assembled such that during being sealed at the outlet-side container, an outlet opening for allowing blood having processed by the filter element to flow out to an outlet flow path in the outlet port at a position 2.4 cm above an end of the lower side portion of the inner seal portion nearer to the effective filtering portion. The outlet opening of the outlet port had a longitudinal dimension of 5 mm and a lateral dimension of 4 mm, and was disposed at the center between the pair of lateral side portions of the inner seal portion. That is, assembly was performed so as to allow the outlet opening and the slit to communicate with each other.

After the total head that is the total of the upstream-side head, the head between the inlet and outlet of the blood processing filter, and the downstream-side head was fixed to 150 cm, 300 g of polyvinylpyrrolidone (weight-average molecular weight of 360000) aqueous solution (Wako Pure Chemical Industries, Ltd. K90) prepared to have a viscosity of 17 mPa·s (25° C.) and pH 3.8 as the liquid to be processed (instead of blood) was injected into the pre-filtration liquid reservoir bag, subsequently 15 mL of air was injected, and the solution was caused to flow by gravity at room temperature. A post-filtration liquid recovery bag was preliminarily placed on an even balance to allow changes in the weight thereof to be verified.

At this time, the time required from the start of flowing the liquid to be processed until the liquid first reaching the inlet of the post-filtration liquid recovery bag was measured, and defined as a priming time (min.). Furthermore, the time required from the start of flowing the liquid to be processed until the entire liquid to be processed in the pre-filtration reservoir bag being discharged, and air injected into the pre-filtration liquid reservoir bag and subsequently reaching the filter to stop increase in weight of the post-filtration liquid recovery bag, that is, the time required to filter the entire liquid was measured, and defined as a total processing time (min.). The weight of the liquid recovered in the post-filtration liquid recovery bag was measured and defined as an amount of recovery (g). An average processing speed (g/min.) was calculated on the basis of the recovery amount and the total processing time, and thus obtained. A difference between the 300 g of liquid that was injected into the post-filtration liquid reservoir bag and the amount of recovery was obtained by calculation, and defined as amount of loss (g).

Comparative Example 1

Comparative Example 1 corresponds to the aforementioned blood processing filter 1E according to the first comparative mode (see FIG. 14). A blood processing filter without the flow path securing sheet and the frame sheet was assembled by the same method as that of Example except that an inlet-side container, a filter element and an outlet-side container were stacked to form an inner seal portion, and subsequently an outside seal portion was formed, and filtration was performed.

Comparative Example 2

Figure 15:
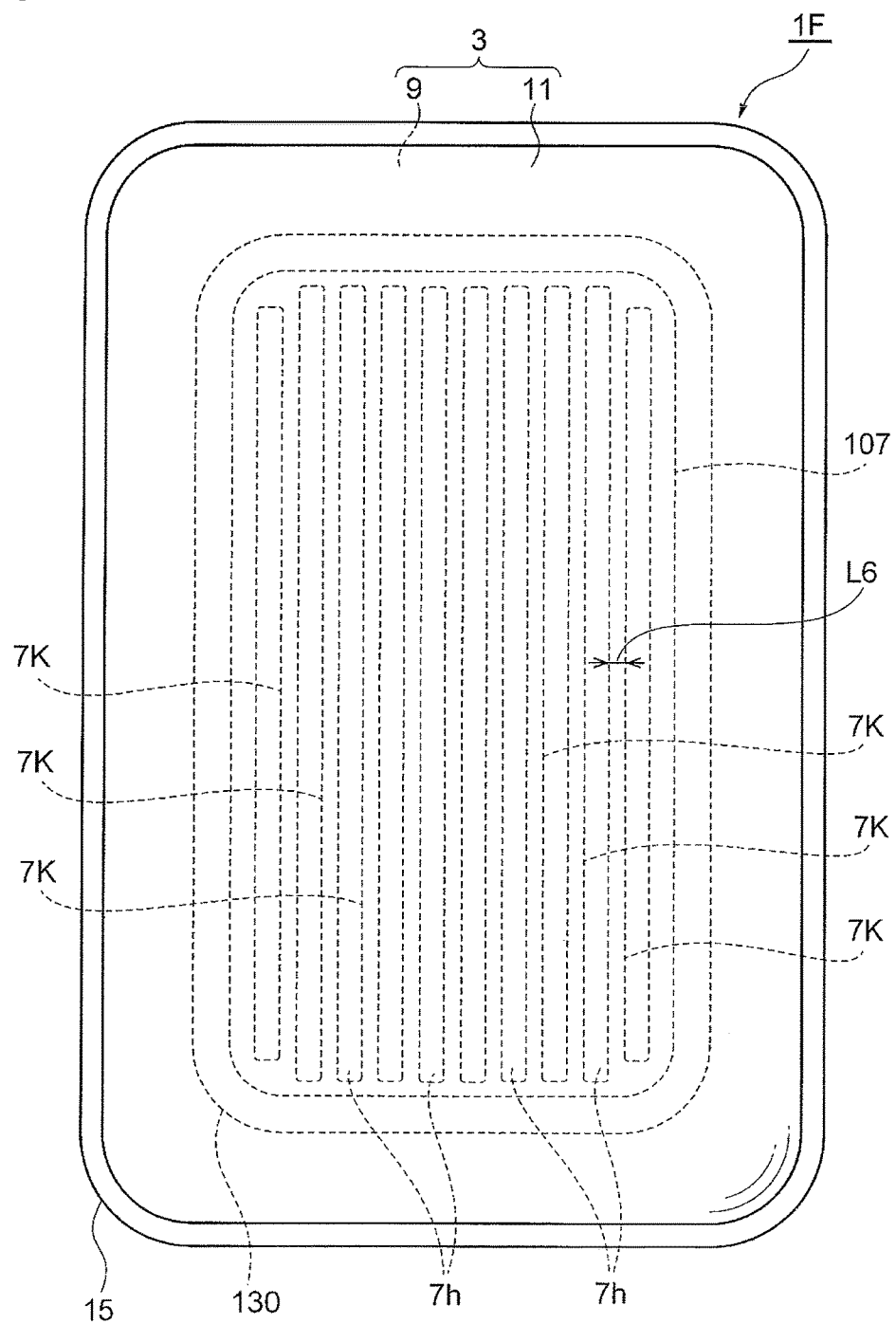
FIG. 15 is a plan view of a blood processing filter according to a second comparative mode.

Comparative Example 2 corresponds to the blood processing filter 1F according to the aforementioned second comparative mode (see FIG. 15). A blood processing filter was assembled by the same method as that of Example except that it had slit-formed flow path holes each having a longitudinal dimension of 72 mm and a width of 3 mm was adopted at eleven sites in the inner seal portion as flow path securing sheet, and filtration was performed. Note that FIG. 15 was shown without the filter element, the inlet port and the outlet port, which were omitted.

The results of Example, Comparative Example 1 and Comparative Example 2 are summarized in Table 1.

TABLE 1

|  | Example | Comparative Example 1 | Comparative Example 2 |
| --- | --- | --- | --- |
| Priming Time (min.) | 2.8 | 2.3 | 2.8 |
| Total Processing Time (min.) | 17.3 | 26.6 | 17.4 |
| Amount of Recovery (g) | 273.2 | 273.6 | 271.2 |
| Average Processing Speed (g/min.) | 15.8 | 10.3 | 15.6 |
| Amount of Loss (g) | 26.8 | 26.4 | 28.8 |

In Example, the total processing time was shortened and the average processing speed was improved in comparison with Comparative Example 1. This is because, through use of the flow path securing sheet in Example, the filter material distant from the outlet port was also effectively utilized, and a situation did not arise in which the outlet opening of the outlet port came into contact with the filter element and was blocked. That is, liquid flowing out from each portion in a planar direction did not concentrate at one point of the outlet port, but flowed in directions diffused by the diffusing openings of the flow path securing sheet, passed through the passage region that corresponded to the inner seal portion and served as a flow path, flowed again into the slits communicating with the outlet opening of the outlet port, and was discharged to the outside of the filter through the outlet port. Furthermore, Example had the structures, such as the inner seal portion and ribs, that made the blood preparation stagnant, but the amount of loss was substantially equivalent to that of Comparative Example 1.

In Example, the amount of loss was reduced in comparison with Comparative Example 2. That is, the collecting rate was improved. This is because in Example, the number of ribs of the flow path securing sheet is small to reduce residue of blood preparation, which was to occur around the ribs. In Example, the priming time, the total processing time and the average processing speed were substantially equivalent to those in Comparative Example 2.

REFERENCE SIGNS LIST 1A, 1B, 1C, 1D . . . Blood processing filter, 5 . . . Filter element, 53 . . . Post-filter layer, 6 . . . Concave portion, 7 . . . Flow path securing sheet, 7a . . . Rib, 7b . . . Slit, 7c . . . Diffusing opening, 9 . . . Inlet-side container (inlet-side flexible container), 9a . . . Inlet port, 10 . . . Frame sheet, 10b . . . First opening (opening), 10c . . . Second opening (opening), 11 . . . Outlet-side container (outlet-side flexible container), 11a . . . Outlet port, 11c . . . Outlet opening, 13 . . . Inner seal portion (first seal portion), 13a . . . Lower side portion (communication portion), 13b . . . upper side portion (communication portion), 13c . . . Lateral side portion (lateral portion), 15 . . . Outside seal portion (second seal portion), L1 . . . Width of outlet opening, L2 . . . Width of slit (interval of pair of ribs), L3 . . . Distance from end of slit to end of lower side portion nearer to slit, L4 . . . Distance from end of diffusing opening to end of lateral side portion nearer to diffusing opening, S . . . Passage region, t . . . Thickness.

The invention claimed is:

1. A blood processing filter comprising:
   a sheet-shaped filter element;
   an inlet-side flexible container and an outlet-side flexible container that sandwich the filter element;
   an inlet port that is provided at the inlet-side flexible container and receives unprocessed blood; and
   an outlet port that is provided at the outlet-side flexible container and discharges the blood processed by the filter element, the filter further comprising:

a flow path securing sheet disposed between the filter element and the outlet-side flexible container;

a belt-shaped first seal portion that seals at least the filter element and the flow path securing sheet, and is provided so as to be apart from the outlet-side flexible container; and an annular second seal portion that seals at least the inlet-side flexible container and the outlet-side flexible container, and is provided so as to surround the filter element and the flow path securing sheet, wherein the first seal portion includes a pair of lateral portions disposed opposite to each other with the outlet port interposed therebetween, and a communication portion connected to the pair of lateral portions, the communication portion includes a lower side portion and an upper side portion, the flow path securing sheet includes ribs consisting of only a pair of ribs that are disposed between the pair of lateral portions and opposite to each other with the outlet port interposed therebetween, a slit disposed between the pair of ribs to communicate with a concave portion formed of the communication portion, and diffusing openings that are disposed outside of the pair of ribs, continuously open from the ribs to the lateral portions and communicate with the concave portion formed of the lateral portions, and continuously open from the lower side portion to the upper side portion, and the width of each of the diffusing openings is 20 to 30 mm.

2. The blood processing filter according to claim 1, wherein the pair of ribs is a straight line, a bent line, a curve, or any combination thereof.

3. The blood processing filter according to claim 1, wherein the lower side portion and the upper side portion are disposed opposite to each other with the outlet port interposed therebetween, and the slit communicates with a concave portion formed of the lower side portion and the upper side portion.

4. The blood processing filter according to claim 1, wherein the pair of ribs have distal ends connected to each other so as to surround the outlet port.

5. The blood processing filter according to claim 1, wherein in the filter element, an effective filtering area of a filtering portion is $20\times10^{-4}$ m$^2$ to $70\times10^{-4}$ m$^2$.

6. The blood processing filter according to claim 1, wherein in the flow path securing sheet, a ratio of a total area of the slit and the diffusing openings to an effective filtering area of a filtering portion of the filter element is 30% to 97%.

7. The blood processing filter according to claim 1, wherein an interval between the pair of ribs is 0.1 to 2 times as large as a width of an outlet opening of the outlet port.

8. The blood processing filter according to claim 7, wherein an interval of the pair of ribs is 0.5 to 10 mm.

9. The blood processing filter according to claim 1, wherein a post-filter layer for securing a flow toward the outlet port is further disposed on a side of the filter element nearer to the flow path securing sheet.

10. The blood processing filter according to claim 9, wherein the post-filter layer is a filter layer formed by stacking one or more sheets of nonwoven fabric with an air permeability of 180 to 300 cc/cm$^2$/sec. and a thickness of 0.2 to 2.0 mm.

11. The blood processing filter according to claim 1, wherein the second seal portion sandwiches and is in close contact with the flow path securing sheet between the inlet-side flexible container and the outlet-side flexible container.

12. The blood processing filter according to claim 1, wherein the first seal portion sandwiches and is in contact with the filter element between the inlet-side flexible container and the flow path securing sheet.

13. The blood processing filter according to claim 1, wherein a thickness of the flow path securing sheet is from 0.1 to 3.5 mm.

14. The blood processing filter according claim 1, wherein a frame sheet having an opening is disposed between the filter element and the inlet-side flexible container.

15. The blood processing filter according to claim 14, wherein the first seal portion is formed by sealing the frame sheet, the filter element and the flow path securing sheet in a belt-shaped manner in a state where the frame sheet and the flow path securing sheet sandwich the filter element.

16. The blood processing filter according to claim 14, wherein the frame sheet and the flow path securing sheet have an identical shape, and are rotationally symmetric to allow the inlet-side flexible container and the outlet-side flexible container to be used in a manner replaced with each other.

17. The blood processing filter according to claim 1, wherein a distance from an end of the slit to an end of the communication portion nearer to the slit is 0 to 4 mm.

18. The blood processing filter according to claim 1, wherein a distance from an end of the diffusing opening to an end of the lateral portion nearer to the diffusing opening is 0 to 4 mm.

19. The blood processing filter according to claim 1, wherein an average processing speed is at least 12.0 g/min.

20. The blood processing filter according to claim 1, wherein a remaining amount of liquid that remains in the blood processing filter after processing is 30.0 g or less.

21. A blood processing method using a blood processing filter, the filter comprising:

a sheet-shaped filter element;

an inlet-side flexible container and an outlet-side flexible container that sandwich the filter element;

an inlet port that is provided at the inlet-side flexible container and receives unprocessed blood; and an outlet port that is provided at the outlet-side flexible container and discharges the blood processed by the filter element, the filter further comprising:

a flow path securing sheet disposed between the filter element and the outlet-side flexible container;

a belt-shaped first seal portion that seals at least the filter element and the flow path securing sheet, and is provided so as to be apart from the outlet-side flexible container; and an annular second seal portion that seals at least the inlet-side flexible container and the outlet-side flexible container, and is provided so as to surround the filter element and the flow path securing sheet, wherein the first seal portion includes a pair of lateral portions disposed opposite to each other with the outlet port interposed therebetween, and a communication portion connected to the pair of lateral portions, the communication portion includes a lower side portion and an upper side portion, the flow path securing sheet includes ribs consisting of only a pair of ribs that are disposed between the pair of lateral portions and opposite to each other with the outlet port interposed therebetween, a slit disposed between the pair of ribs to communicate with a concave portion formed of the communication portion, and diffusing openings that are disposed outside of the pair of ribs and continuously open from the ribs to the lateral portions and communicate with the concave portion formed of the lateral portions, and continuously open from the lower side portion to the upper side portion, and the width of each of the diffusing openings is 20 to 30 mm.

22. The blood processing method according to claim 21, wherein the blood processing filter includes a post-filter layer for securing a flow toward the outlet port, on a side of the filter element nearer to the flow path securing sheet, and from among flows of the blood flowing in the post-filter layer, a flow in a direction toward the outlet port is formed in a region overlaid on the slit, and a flow more diffusing than that in the region overlaid on the slit is formed in a region overlaid on the diffusing openings.

23. The blood processing method according to claim 21, wherein leukocytes are removed.

* * * * *